United States Patent
Morrison et al.

(10) Patent No.: US 9,635,901 B1
(45) Date of Patent: May 2, 2017

(54) FOOTWEAR WITH INTERCHANGEABLE SOLE STRUCTURE ELEMENTS

(71) Applicant: NIKE, Inc., Beaverton, OR (US)

(72) Inventors: Catherine F. Morrison, Portland, OR (US); Scott C. Holt, Portland, OR (US); Dervin A. James, Hillsboro, OR (US); Ty A. Ransom, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 14/887,769

(22) Filed: Oct. 20, 2015

(51) Int. Cl.
| | |
|---|---|
| *A43B 3/00* | (2006.01) |
| *A43B 7/14* | (2006.01) |
| *A43B 13/16* | (2006.01) |
| *A61B 5/103* | (2006.01) |
| *A43B 13/36* | (2006.01) |
| *A43B 3/24* | (2006.01) |

(52) U.S. Cl.
CPC .......... *A43B 7/1465* (2013.01); *A43B 3/0005* (2013.01); *A43B 3/24* (2013.01); *A43B 13/16* (2013.01); *A43B 13/36* (2013.01); *A61B 5/1036* (2013.01)

(58) Field of Classification Search
CPC ......... A43B 3/0005; A43B 3/24; A43B 3/146; A43B 13/36
USPC ............................................ 36/100, 15, 136
See application file for complete search history.

(56) References Cited

U.S. PATENT DOCUMENTS

| | | |
|---|---|---|
| 4,680,875 A | 7/1987 | Danieli |
| 4,814,661 A | 3/1989 | Ratzlaff et al. |
| 4,905,383 A | 3/1990 | Beckett et al. |
| 5,014,706 A | 5/1991 | Philipp |
| 5,282,288 A | 2/1994 | Henson |
| 5,797,199 A | 8/1998 | Miller et al. |
| 5,813,142 A | 9/1998 | Demon |
| 6,578,291 B2 * | 6/2003 | Hirsch ................ A43B 3/0005 36/132 |
| 6,976,323 B1 | 12/2005 | Halliday |
| 7,210,251 B1 | 5/2007 | Rolle |

(Continued)

FOREIGN PATENT DOCUMENTS

GB          2498196 A       7/2013

OTHER PUBLICATIONS

U.S. Appl. No. 14/887,761, titled Footwear with Interchangeable Sole Structure Elements, filed Oct. 20, 2015.

(Continued)

*Primary Examiner* — Marie Bays
(74) *Attorney, Agent, or Firm* — Banner & Witcoff, Ltd

(57) ABSTRACT

A shoe may comprise an upper and a sole structure that includes a plurality of support elements located in a plantar region. Each of the support elements may be non-destructively removable from and replaceable into the sole structure. The shoe may comprise a plurality of sensors configured to measure force exerted in a footbed region of the article of footwear, as well as a processor communicatively coupled to the sensors. The processor may be configured to receive input indicative of forces measured by the sensors and to transmit data based on that input. Methods utilizing the article may include removing a support element and replacing the removed support element with a replacement support element.

25 Claims, 16 Drawing Sheets

(56) References Cited

U.S. PATENT DOCUMENTS

| | | | |
|---|---|---|---|
| 7,334,350 B2* | 2/2008 | Ellis, III | A43B 3/0005 36/100 |
| 7,377,055 B2 | 5/2008 | Bramani | |
| 7,426,873 B1 | 9/2008 | Kholwadwala et al. | |
| 7,493,230 B2 | 2/2009 | Schwartz et al. | |
| 7,596,891 B2 | 10/2009 | Carnes et al. | |
| 7,607,243 B2 | 10/2009 | Berner, Jr. et al. | |
| 7,644,522 B2 | 1/2010 | Ramirez | |
| 7,676,961 B2 | 3/2010 | DiBenedetto et al. | |
| 7,707,742 B2 | 5/2010 | Ellis, III | |
| 7,770,306 B2 | 8/2010 | Lyden | |
| 7,771,371 B2 | 8/2010 | Avni | |
| 7,793,430 B2 | 9/2010 | Ellis | |
| 7,814,682 B2 | 10/2010 | Grove et al. | |
| 7,866,064 B2 | 1/2011 | Gerber | |
| 7,908,768 B2 | 3/2011 | Cheskin et al. | |
| 7,997,012 B2 | 8/2011 | Hoffer et al. | |
| 8,209,883 B2 | 7/2012 | Lyden | |
| 8,215,037 B2 | 7/2012 | James | |
| 8,356,426 B1 | 1/2013 | Daniel et al. | |
| 8,571,827 B2* | 10/2013 | Jang | A43B 3/0005 340/669 |
| 8,646,191 B2* | 2/2014 | Amos | A43B 7/1425 36/103 |
| 8,763,276 B2* | 7/2014 | Greene | A43D 35/00 36/15 |
| 8,978,275 B2 | 3/2015 | James | |
| 2003/0009308 A1 | 1/2003 | Kirtley | |
| 2006/0005426 A1 | 1/2006 | Votolato | |
| 2006/0016255 A1* | 1/2006 | Haselhurst | A43B 3/0005 73/172 |
| 2006/0059726 A1 | 3/2006 | Song et al. | |
| 2007/0006489 A1 | 1/2007 | Case et al. | |
| 2007/0039209 A1 | 2/2007 | White et al. | |
| 2007/0266597 A1 | 11/2007 | Jones | |
| 2009/0049712 A1 | 2/2009 | Steszyn et al. | |
| 2009/0267783 A1* | 10/2009 | Vock | A43B 1/0036 340/669 |
| 2009/0278707 A1* | 11/2009 | Biggins | A43B 1/0027 340/870.16 |
| 2010/0024251 A1* | 2/2010 | Delgatty | A43B 1/0027 36/101 |
| 2010/0063778 A1* | 3/2010 | Schrock | A43B 3/00 702/188 |
| 2010/0063779 A1 | 3/2010 | Schrock et al. | |
| 2010/0122473 A1 | 5/2010 | Santos | |
| 2010/0192415 A1 | 8/2010 | James | |
| 2010/0199524 A1 | 8/2010 | Grun et al. | |
| 2010/0306894 A1 | 12/2010 | Calvert | |
| 2010/0313449 A1 | 12/2010 | Brown | |
| 2010/0324455 A1 | 12/2010 | Rangel et al. | |
| 2011/0175744 A1 | 7/2011 | Englert et al. | |
| 2011/0275956 A1 | 11/2011 | Son et al. | |
| 2012/0023776 A1 | 2/2012 | Skaja et al. | |
| 2012/0066938 A1 | 3/2012 | French et al. | |
| 2012/0222332 A1 | 9/2012 | Greene et al. | |
| 2012/0234111 A1 | 9/2012 | Molyneux et al. | |
| 2013/0213147 A1 | 8/2013 | Rice et al. | |
| 2014/0223779 A1 | 8/2014 | Elder et al. | |
| 2014/0283412 A1 | 9/2014 | Elder et al. | |

OTHER PUBLICATIONS

International Search Report and Written Opinion of PCT/US2016/052419 mailed Jan. 3, 2017.

International Search Report and Written Opinion for PCT/US2016/052421 mailed Jan. 3, 2017.

* cited by examiner

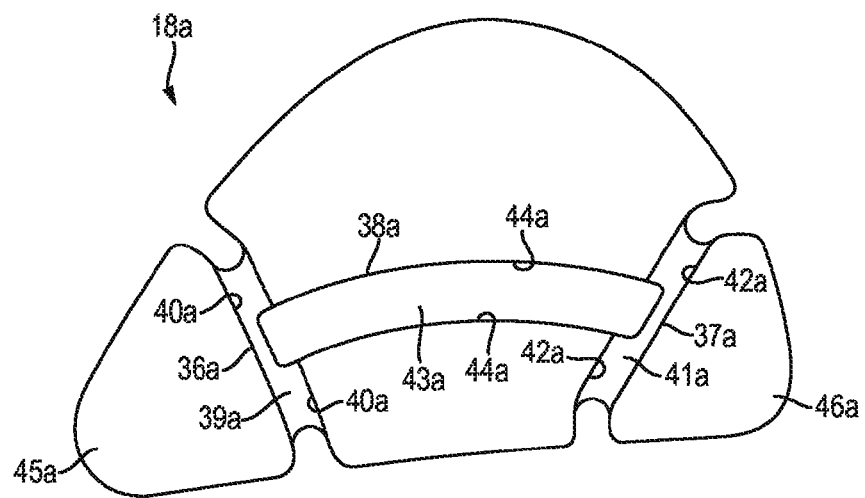
FIG. 5A1
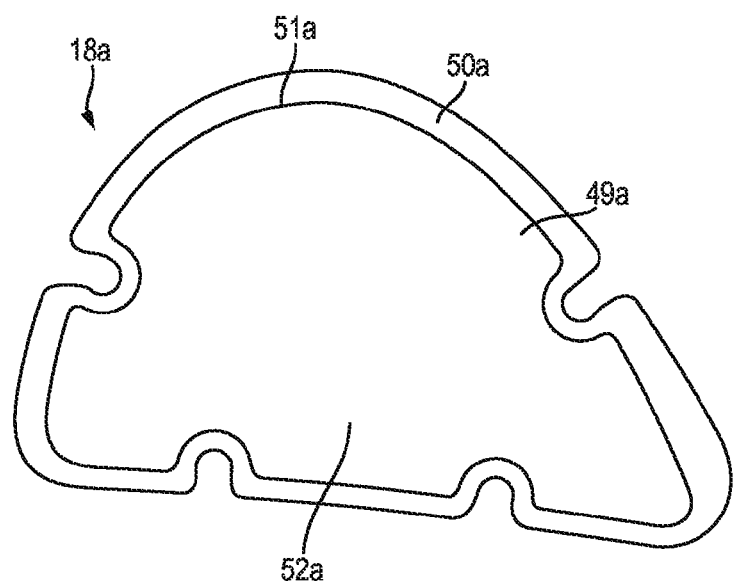
FIG. 5A2

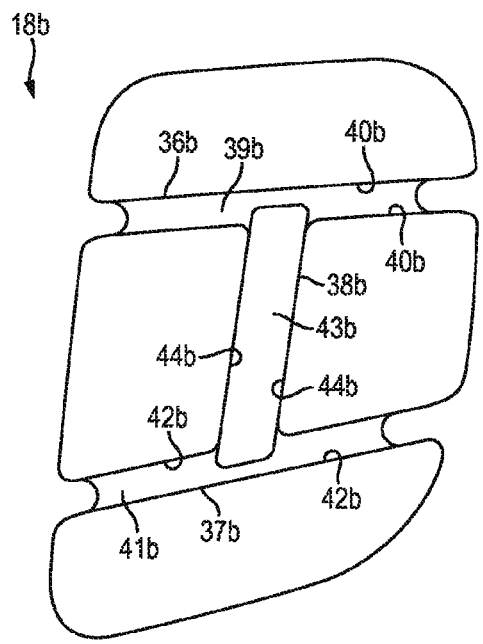
FIG. 5B1
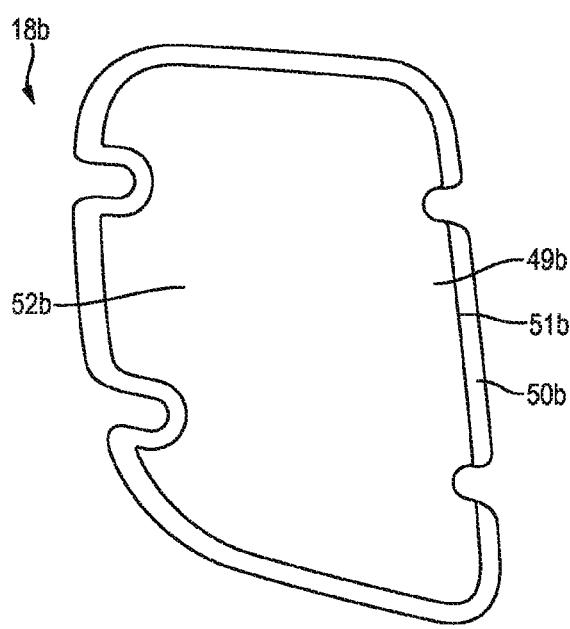
FIG. 5B2

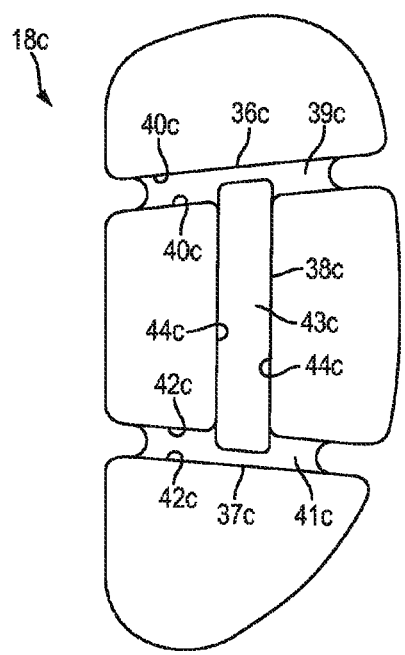
FIG. 5C1
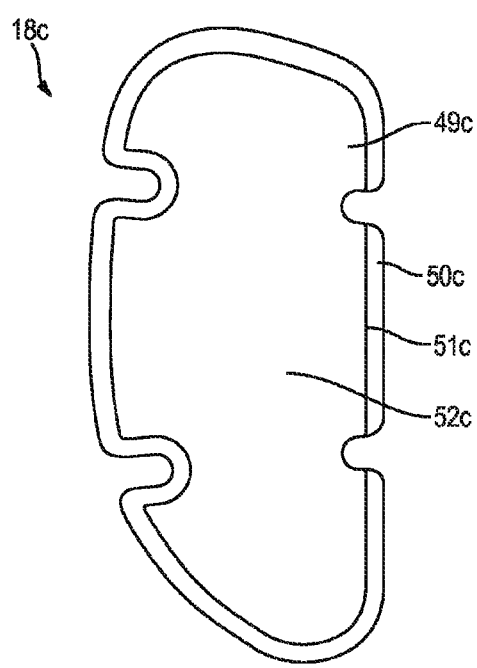
FIG. 5C2

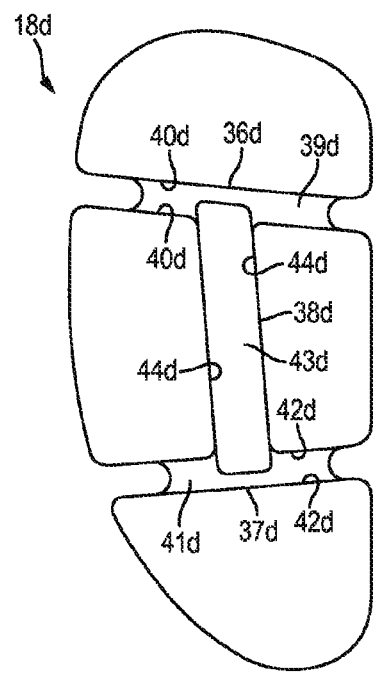
FIG. 5D1
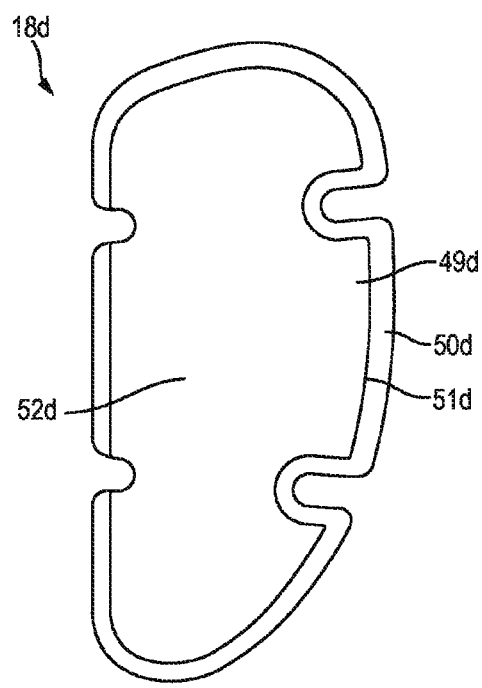
FIG. 5D2

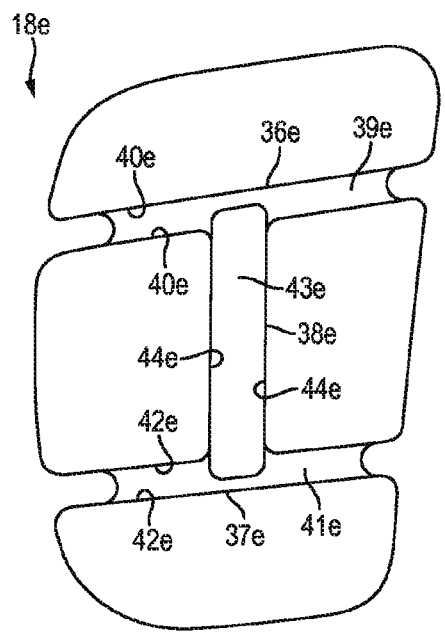
FIG. 5E1
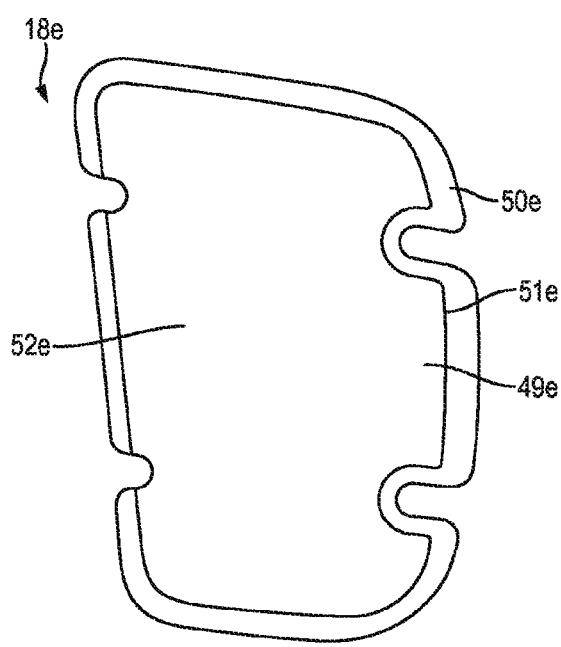
FIG. 5E2

US 9,635,901 B1

FOOTWEAR WITH INTERCHANGEABLE SOLE STRUCTURE ELEMENTS

BACKGROUND

Conventional articles of footwear generally include an upper and a sole structure. The upper provides a covering for the foot and securely positions the foot relative to the sole structure. The sole structure is secured to a lower portion of the upper and is configured so as to be positioned between the foot and the ground when a wearer is standing, walking, or running. The sole structure may include one or more cushioning elements. Those cushioning elements may help to attenuate and dissipate forces on a wearer foot that may result from ground impact during walking or running.

Conventionally, sole structures have been designed based on a particular condition or set of conditions, and/or based on a particular set of preferences and/or characteristics of a targeted shoe wearer. For example, cushioning structure may be sized and located based on expected movements of a shoe wearer associated with a particular type of sport. In many cases, the choice of cushioning structure may be a compromise among numerous possible alternatives. Because of variations among different individuals who might wear a particular shoe, however, some individuals may find a particular compromise to be less than satisfactory. A sole structure that allows adjustment of cushioning characteristics to better match the preferences and/or needs of an individual wearer is thus desirable.

BRIEF DESCRIPTION OF THE DRAWINGS

Some embodiments are illustrated by way of example, and not by way of limitation, in the figures of the accompanying drawings and in which like reference numerals refer to similar elements.

FIGS. 5A1 and 5A2 are respective bottom and top views of a toe forefoot support element of the shoe from FIG. 1.

FIGS. 5B1 and 5B2 are respective bottom and top views of a medial forefoot support element of the shoe from FIG. 1.

FIGS. 5C1 and 5C2 are respective bottom and top views of a medial heel support element of the shoe from FIG. 1.

FIGS. 5D1 and 5D2 are respective bottom and top views of a lateral heel support element of the shoe from FIG. 1.

FIGS. 5E1 and 5E2 are respective bottom and top views of a lateral forefoot support element of the shoe from FIG. 1.

DETAILED DESCRIPTION

Figure 1:
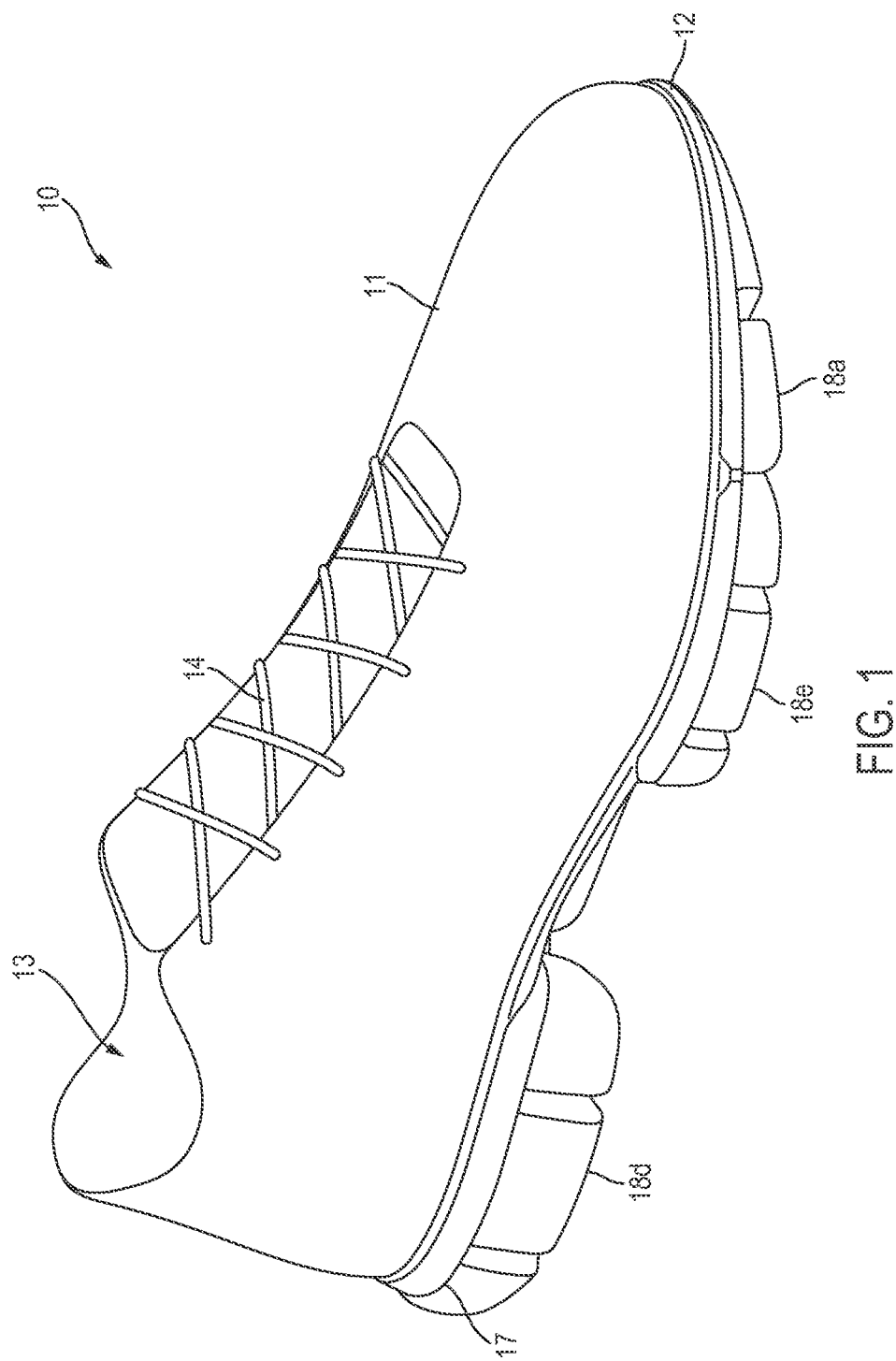
FIG. 1 is a front lateral perspective view of a shoe according to some embodiments.

In some embodiments, an article of footwear may include a sole structure having multiple independently removable and replaceable support elements. A user may customize the article to meet his or her preferences and/or needs by choosing a combination of support elements having desired properties. In some embodiments, for example, a user may remove some or all support elements previously installed and replace the removed support elements with support elements having different characteristics.

In some embodiments, an article of footwear includes an upper and a sole structure. The sole structure may include a plurality of support elements located in a plantar region. Each of the support elements may be at least partially secured in a corresponding position on the sole structure by a corresponding retaining band, with each of those retaining bands surrounding at least a portion of its corresponding support element. The retaining bands may be elastically and non-destructively expandable.

In some embodiments, an article of footwear may include an upper and a sole structure, with the sole structure including a base having a plurality of positions defined therein. A plurality of support elements may respectively correspond to and be located in those positions. Elastic retaining bands may secure the support elements in their corresponding positions.

In some embodiments, an article of footwear may comprise an upper and a plurality of sensors positioned within the article of footwear and configured to measure force exerted in a footbed region of the article of footwear. The article of footwear may further comprise a processor communicatively coupled to the sensors. The processor may be configured to receive input indicative of forces measured by the sensors and to transmit data based on the input indicative of forces measured by the sensors. The article of footwear may additionally comprise a sole structure that includes a plurality of support elements located in a plantar region, wherein each of the support elements is non-destructively removable from and replaceable into the sole structure.

In some embodiments, a method may include a step of holding an article of footwear that comprises an upper and a sole structure. The sole structure may include a plurality of support elements located in a plantar region. Each of the support elements may be at least partially secured in a corresponding position on the sole structure by a corresponding retaining band, with each of the retaining bands being elastically and non-destructively expandable. The method may further include removing one of the support elements from the sole structure and securing a replacement support element into the position corresponding to the removed support element.

In some embodiments, a method may comprise receiving a data transmission from an article of footwear. The article of footwear may comprise an upper, a plurality of sensors positioned within the article of footwear and configured to measure forces exerted in a footbed region of the article of footwear, and a processor. The processor may be communicatively coupled to the sensors. The processor may be configured to receive input indicative of forces measured by the sensors and to transmit data based on the input indicative of forces measured by the sensors. The article of footwear may also comprise a sole structure including a plurality of support elements located in a plantar region, each of the support elements being non-destructively removable from and replaceable into the sole structure. The method may include identifying, in response to the received data transmission, a support element for replacement, removing the identified support element from the article of footwear, and replacing the removed support element with a replacement support element.

In some embodiments a kit may comprise an article of footwear that includes an upper and a sole structure base. The sole structure base may include a plurality of positions defined therein. The kit may further comprise a plurality of first position support elements corresponding to a first of the positions. Each of the first position support elements may be configured for placement into the first position and for securing in the first position by a first retaining band coupled to the base and corresponding to the first position. The first retaining band may be elastically and non-destructively expandable. The kit may additionally comprise a plurality of second position support elements corresponding to a second of the positions. Each of the second position support elements may be configured for placement into the second position and for securing in the second position by a second retaining band coupled to the base and corresponding to the second position. The second retaining band may be elastically and non-destructively expandable.

In some embodiments, a kit may comprise an article of footwear comprising an upper, a sole structure base having a plurality of positions defined therein, a plurality of sensors positioned within the article of footwear and configured to measure forces exerted in a footbed region of the article of footwear, and a processor. The processor may be communicatively coupled to the sensors, and the processor may be configured to receive input indicative of forces measured by the sensors and to transmit data based on the input indicative of forces measured by the sensors. The kit may additionally comprise a plurality of first position support elements corresponding to a first of the positions, each of the first position support elements configured for placement into, securing in, and non-destructive removal from the first position. The kit may further comprise a plurality of second position support elements corresponding to a second of the positions, each of the second position support elements configured for placement into, securing in, and non-destructive removal from the second position.

Additional embodiments are described herein.

To assist and clarify subsequent description of various embodiments, various terms are defined herein. Unless context indicates otherwise, the following definitions apply throughout this specification (including the claims). "Shoe" and "article of footwear" are used interchangeably to refer to an article intended for wear on a human foot. A shoe may or may not enclose the entire foot of a wearer. For example, a shoe could include a sandal-like upper that exposes large portions of a wearing foot. The "interior" of a shoe refers to space that is occupied by a wearer's foot when the shoe is worn. An interior side, surface, face, or other aspect of a shoe component refers to a side, surface, face or other aspect of that component that is (or will be) oriented toward the shoe interior in a completed shoe. An exterior side, surface, face or other aspect of a component refers to a side, surface, face or other aspect of that component that is (or will be) oriented away from the shoe interior in the completed shoe. In some cases, the interior side, surface, face or other aspect of a component may have other elements between that interior side, surface, face or other aspect and the interior in the completed shoe. Similarly, an exterior side, surface, face or other aspect of a component may have other elements between that exterior side, surface, face or other aspect and the space external to the completed shoe.

Shoe elements can be described based on regions and/or anatomical structures of a human foot wearing that shoe, and by assuming that the interior of the shoe generally conforms to and is otherwise properly sized for the wearing foot. A forefoot region of a foot includes the heads and bodies of the metatarsals, as well as the phalanges. A forefoot element of a shoe is an element having one or more portions located under, over, to the lateral and/or medial side of, and/or in front of a wearer's forefoot (or portion thereof) when the shoe is worn. A midfoot region of a foot includes the cuboid, navicular, and cuneiforms, as well as the bases of the metatarsals. A midfoot element of a shoe is an element having one or more portions located under, over, and/or to the lateral and/or medial side of a wearer's midfoot (or portion thereof) when the shoe is worn. A heel region of a foot includes the talus and the calcaneus. A heel element of a shoe is an element having one or more portions located under, to the lateral and/or medial side of, and/or behind a wearer's heel (or portion thereof) when the shoe is worn. The forefoot region may overlap with the midfoot region, as may the midfoot and heel regions.

Unless indicated otherwise, a longitudinal axis refers to a horizontal heel-toe axis along the center of the foot that is roughly parallel to a line along the second metatarsal and second phalanges. A transverse axis refers to a horizontal axis across the foot that is generally perpendicular to a longitudinal axis. A longitudinal direction is generally parallel to a longitudinal axis. A transverse direction is generally parallel to a transverse axis. "Top," "bottom," and other terms indicating a vertical direction assume that surfaces of a sole structure intended for ground contact are resting on a horizontal surface, and that the sole structure is not deformed.

Throughout the following detailed description and in the accompanying drawing figures, multiple components, portions, regions, or other items may be identified using a common reference number, but with different letters appended to distinguish among specific individual items. For example, embodiments include an article of footwear having a sole structure that includes five support elements 18*a*, 18*b*, 18*c*, 18*d*, and 18*e*. Items identified in this manner may be identified collectively using only the number portion of the reference (e.g., "support elements 18"). A number portion of such references may also be used to generically identify one or more of those items (e.g., "a support element 18," "one or more support elements 18").

FIG. 1 is a front lateral perspective view of a shoe 10 according to some embodiments. The medial side of shoe 10 has a similar configuration and appearance, but is configured to correspond to a medial side of a wearer foot. Shoe 10 is configured for wear on a right foot and is part of a pair that includes a shoe (not shown) that is a mirror image of shoe 10 and is configured for wear on a left foot.

Shoe 10 includes an upper 11 coupled to a sole structure 12. Upper 11 may be of conventional construction and formed from any of various types or materials and have any of a variety of different constructions. Upper 11 includes an ankle opening 13 through which a wearer foot may be inserted into an interior void formed in part by upper 11. A lace 14 passes through eyelets on either side of a tongue opening and may be cinched to secure shoe 10 to a wearer foot. Upper 11 may be lasted by stitching bottom edges of upper 11 to a strobel (not shown) or other lasting element so as to enclose the foot-receiving interior void of shoe 10. In other embodiments, a shoe may include a sole structure similar to sole structure 12, but with an upper different from that of shoe 10. For example, an upper may be a sandal-like arrangement of straps. As another example, an upper may utilize one or more closure mechanisms other than or in addition to a lace.

Sole structure 12 includes a base 17 and five support elements 18. Only support elements 18a, 18e, and 18d are visible in FIG. 1. Two additional support elements 18b and 18c are visible in subsequent drawings and are described below. As also explained in more detail below, each of support elements 18 is non-destructively removable from and replaceable into base 17 independently of each of the other support elements 18. Bottom surfaces of support elements 18 form ground-contacting surfaces of sole structure 12.

As explained in more detail below, sole structure 12 includes a sensor assembly attached to a top surface of base 17, as well as an electronics module that rests within a well formed in the midfoot region of base 17. In the embodiment of shoe 10, a bottom surface of the lasting element sewn to the bottom edges of upper 11 is directly attached to a top surface of the sensor assembly, as well as to surrounding portions of the base 17 top surface not covered by the sensor assembly. A raised outer edge surrounding the top surface of base 17 is bonded to lower regions of upper 11. The top surface and raised outer edge of base 17 are further described below in connection with FIGS. 6 and 7. In other embodiments, an upper may be coupled to a sole structure in another manner. For example, a midsole may be interposed between a base and a lasting element attached to an upper.

Figure 2:
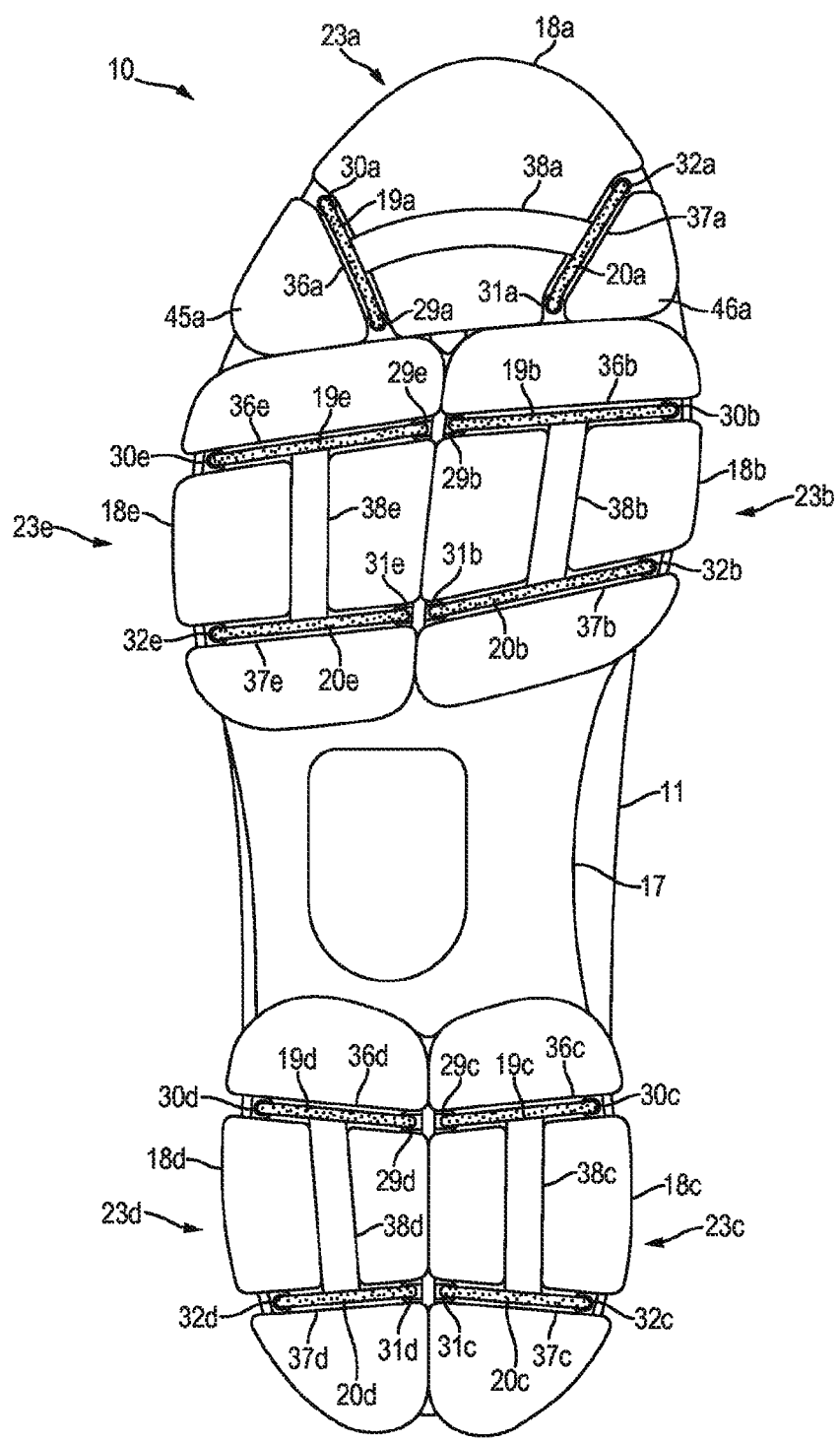
FIG. 2 is a bottom view of the shoe from FIG. 1.

FIG. 2 is a bottom view of shoe 10 showing all of support elements 18. Toe forefoot support element 18a is secured to the underside of base 17 in a toe forefoot position 23a by elastic retaining bands 19a and 20a. Medial forefoot support element 18b is secured to the underside of base 17 in a medial forefoot position 23b by elastic retaining bands 19b and 20b. Medial heel support element 18c is secured to the underside of base 17 in a medial heel position 23c by elastic retaining bands 19c and 20c. Lateral heel support element 18d is secured to the underside of base 17 in a lateral heel position 23d by elastic retaining bands 19d and 20d. Lateral forefoot support element 18e is secured to the underside of base 17 in a lateral forefoot position 23e by elastic retaining bands 19e and 20e. In the embodiment of shoe 10, a portion of the base 17 bottom side in a midfoot region is not covered by support elements and remains exposed. In other embodiments, portions of a base bottom side in other regions may also or alternatively be exposed. In still other embodiments, all of a base bottom surface may be covered by support elements.

Figure 3:
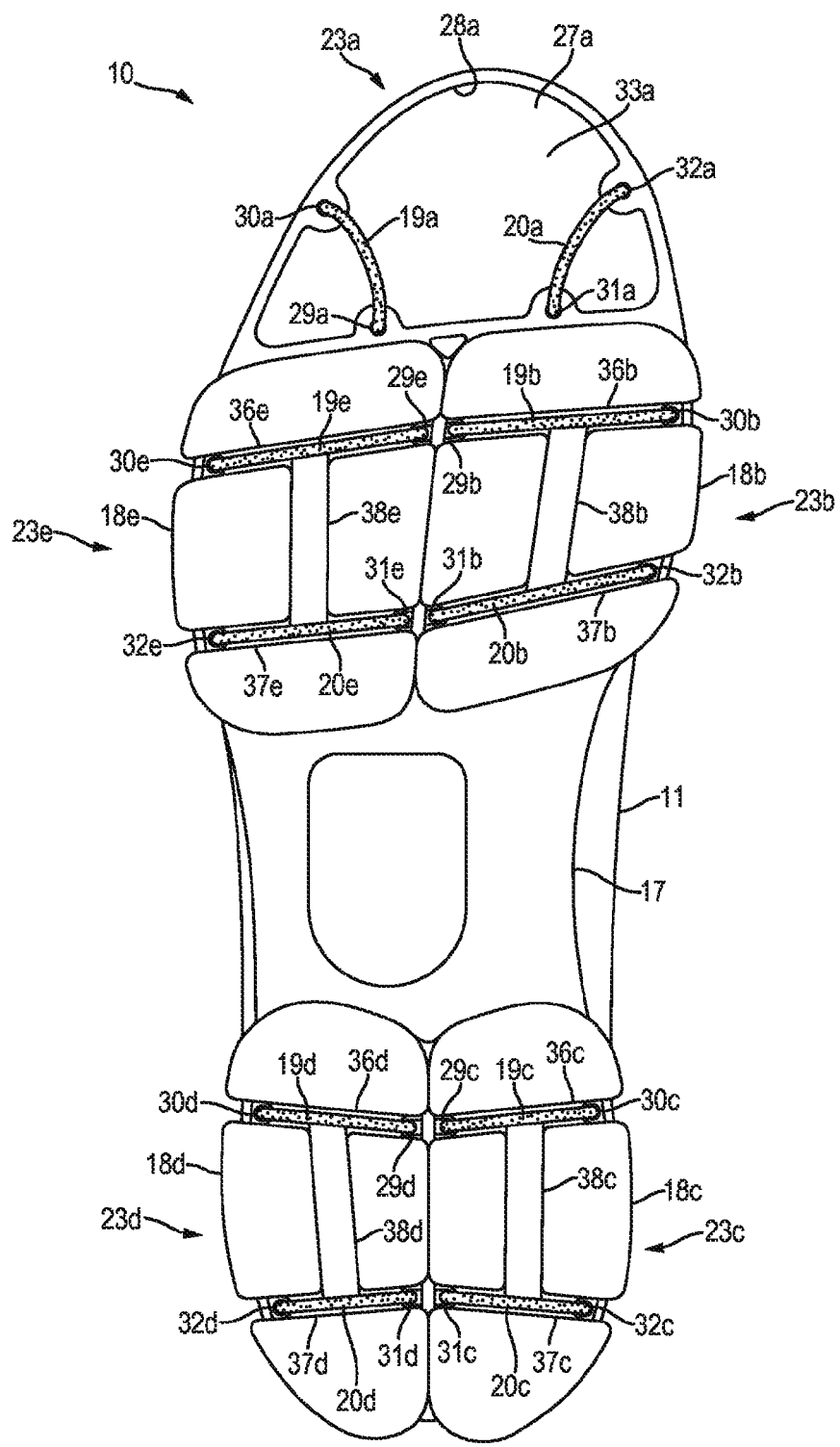
FIG. 3 is a bottom view of the shoe from FIG. 1, and with one of multiple independent support elements removed.

Each of support elements 18 is nondestructively removable from, and replaceable into, its corresponding position on the bottom of base 17. For example, bands 19a and 20a can be expanded out of retaining grooves 36a and 37a, thereby permitting removal of support element 18a. FIG. 3 is a bottom view of shoe 10 showing sole structure 12 after removal of support element 18a from toe forefoot position 23a. Support element 18a, or a replacement support element having a shape that is the same as or similar to that of support element 18a, can be put into position 23a by expanding bands 19a and 20a to accommodate ends of support element 18a (or of a replacement support element) and by then allowing bands 19a and 20a to contract into retaining grooves 36a and 37a (or into similar retaining grooves of a replacement support element). Each of the other support elements 18b through 18e can be removed and reinstalled (or replaced) in a similar manner, either individually or in combination with one or more other support elements 18.

Figure 4:
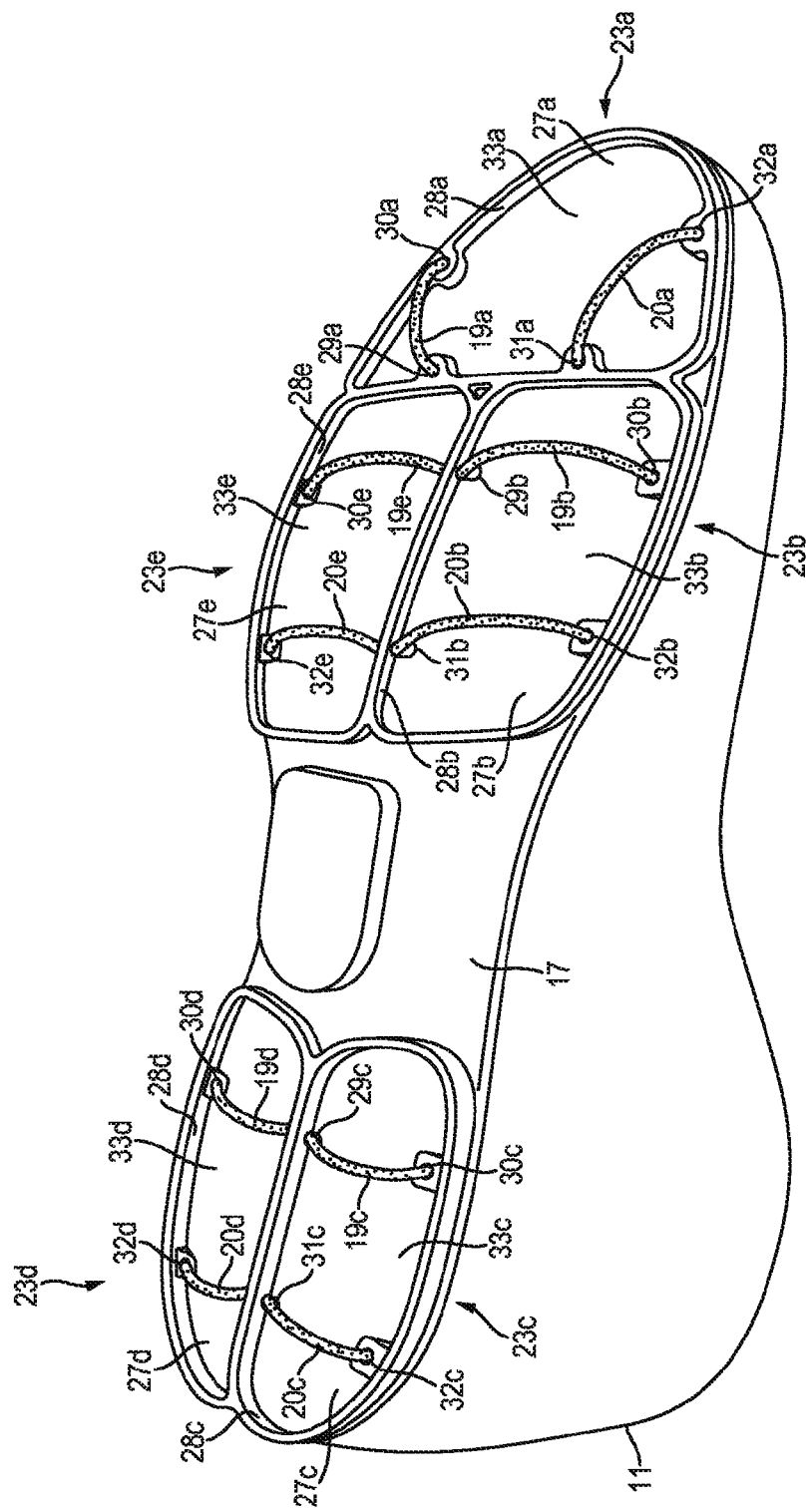
FIG. 4 is a bottom medial perspective view of the shoe from FIG. 1, and with all support elements removed.

FIG. 4 is a bottom medial perspective view of shoe 10. In FIG. 4, all support elements 18 are removed to expose base 17 at each of support element positions 23a through 23e. Each of positions 23 includes features formed in the bottom of base 17 that help retain a corresponding support element 18. Toe forefoot position 23a includes a cavity 27a defined by an interior surface 33a and a surrounding side wall 28a. Medial forefoot position 23b includes a cavity 27b defined by an interior surface 33b and a surrounding side wall 28b. Medial heel position 23c includes a cavity 27c defined by an interior surface 33c and a surrounding side wall 28c. Lateral heel position 23d includes a cavity 27d defined by an interior surface 33d and a surrounding side wall 28d. Lateral forefoot position 23e includes a cavity 27e defined by an interior surface 33e and a surrounding side wall 28e. In some embodiments, base 17 with cavities 27a through 27e may be molded as a single unit from thermoplastic polyurethane (TPU) or other polymer.

Each of positions 23a through 23e includes elastic retaining bands to hold a support element in that position, and which may be elastically and nondestructively expanded to permit repeated removal and installation of support elements. Retaining bands 19a and 20a are located at position 23a. Retaining band 19a extends from holes 29a and 30a and retaining band 20a extends from holes 31a and 32a. Retaining bands 19b and 20b are located at position 23b. Retaining band 19b extends from holes 29b and 30b and retaining band 20b extends from holes 31b and 32b. Retaining bands 19c and 20c are located at position 23c. Retaining band 19c extends from holes 29c and 30c and retaining band 20c extends from holes 31c and 32c. Retaining bands 19d and 20d are located at position 23d. Retaining band 19d extends from holes 29d and 30d and retaining band 20d extends from holes 31d and 32d. Retaining bands 19e and 20e are located at position 23e. Retaining band 19e extends from holes 29e and 30e and retaining band 20e extends from holes 31e and 32e. Retaining bands 19 and retaining bands 20 may be formed from synthetic rubber or other elastic material.

FIGS. 5A1 through 5E2 depict individual support elements 18. In each of FIGS. 5A1 through 5E2, the depictions of support elements 18 are enlarged relative to depictions of support elements 18 in other drawing figures.

FIG. 5A1 is a bottom view of support element 18a removed from sole structure 12. Support element 18a includes two retaining band grooves 36a and 37a. An additional groove 38a connects grooves 36a and 37a. Each of grooves 36a, 37a, and 38a includes a recessed floor (39a, 41a, 43a) surrounded by side walls (40a, 42a, 44a). Recessed floor 43a may be slightly deeper than portions of floors 39a and 41a outside of the intersections of grooves 36a and 37a with groove 38a.

Grooves 36a and 37a respectively correspond to retaining bands 19a and 20a. In particular, retaining band 19a rests within groove 36a and retaining band 20a rests within groove 37a when support element 18a is installed in position 23a of sole structure 12. Groove 38a allows additional flexibility and articulation of support element 18a. Groove 38a also permits easier access to retaining bands 19a and 20a when support element 18a is installed in position 23a. For example, a wearer of shoe 10 may slide a tip of a flat head screwdriver, or a similarly shaped tool, along floor 43*a* of groove 38*a* and under a portion of retaining band 19*a* at the intersection of grooves 36*a* and 38*a*. Using the tool, the wearer may then lift and expand retaining band 19*a* out of groove 36*a*, and slide expanded retaining band 19*a* over the edges of outer side wall 40*a*. The wearer may then slide expanded retaining band 19*a* over the lateral end 45*a* of element 18*a*. In a similar manner, the wearer may use the tool to lift and expand retaining band 20*a* out of groove 37*a*, slide expanded retaining band 20*a* over the edges of outer side wall 42*a*, and slide expanded retaining band 20*a* over the medial end 46*a* of element 18*a* (and/or move element 18*a* from under expanded retaining band 20*a*).

FIG. 5A2 is a top view of support element 18*a* removed from sole structure 12. A narrowed top portion 49*a* of support element 18*a* is defined by a shoulder 50*a* and an inset wall 51*a*. Shoulder 50*a* and inset wall 51*a* surround the perimeter of the top portion of element 18*a*. Narrowed top portion 49*a* nests snugly within cavity 27*a* of position 23*a*. In particular, the outline of inset wall 51*a* has a shape that corresponds to the shape of the outline of side wall 28*a*, the top face 52*a* of element 18*a* has a contour that corresponds to the contour of interior surface 33*a*, and the heights of inset wall 51*a* and side wall 28*a* at locations along their boundaries are matched so that top face 52*a* may contact interior surface 33*a*. Element 18*a* may be installed in position 23*a* by sliding band 19*a* over the lateral end of element 18*a* and into groove 36*a*, sliding band 20*a* over the medial end of element 18*a* and into groove 37*a*, and pressing narrowed top portion 49*a* into cavity 27*a*.

FIGS. 5B1 and 5B2 are respective bottom and top views of support element 18*b* removed from sole structure 12. Support element 18*b* includes two retaining band grooves 36*b* and 37*b* connected by an additional groove 38*b*. Each of grooves 36*b*, 37*b*, and 38*b* includes a recessed floor (39*b*, 41*b*, 43*b*) surrounded by side walls (40*b*, 42*b*, 44*b*). Recessed floor 43*b* may be slightly deeper than portions of floors 39*b* and 41*b* outside of the intersections of grooves 36*b* and 37*b* with groove 38*b*. A narrowed top portion 49*b* of support element 18*b* is defined by a shoulder 50*b* and an inset wall 51*b*. Shoulder 50*b* and inset wall 51*b* surround the perimeter of the top portion of element 18*b*. Narrowed top portion 49*b* nests snugly within cavity 27*b* of position 23*b*. The outline of inset wall 51*b* has a shape that corresponds to the shape of the outline of side wall 28*b*, the top face 52*b* of element 18*b* has a contour that corresponds to the contour of interior surface 33*b*, and the heights of inset wall 51*b* and side wall 28*b* at locations along their boundaries are matched so that top face 52*b* may contact interior surface 33*b*. When support element 18*b* is installed on base 17 in position 23*b*, bands 19*b* and 20*b* respectively rest within grooves 36*b* and 37*b*.

FIGS. 5C1 and 5C2 are respective bottom and top views of support element 18*c* removed from sole structure 12. Support element 18*c* includes two retaining band grooves 36*c* and 37*c* connected by an additional groove 38*c*. Each of grooves 36*c*, 37*c*, and 38*c* includes a recessed floor (39*c*, 41*c*, 43*c*) surrounded by side walls (40*c*, 42*c*, 44*c*). Recessed floor 43*c* may be slightly deeper than portions of floors 39*c* and 41*c* outside of the intersections of grooves 36*c* and 37*c* with groove 38*c*. A narrowed top portion 49*c* of support element 18*c* is defined by a shoulder 50*c* and an inset wall 51*c*. Shoulder 50*c* and inset wall 51*c* surround the perimeter of the top portion of element 18*c*. Narrowed top portion 49*c* nests snugly within cavity 27*c* of position 23*c*. The outline of inset wall 51*c* has a shape that corresponds to the shape of the outline of side wall 28*c*, the top face 52*c* of element 18*c* has a contour that corresponds to the contour of interior surface 33*c*, and the heights of inset wall 51*c* and side wall 28*c* at locations along their boundaries are matched so that top face 52*c* may contact interior surface 33*c*. When support element 18*c* is installed on base 17 in position 23*c*, bands 19*c* and 20*c* respectively rest within grooves 36*c* and 37*c*.

FIGS. 5D1 and 5D2 are respective bottom and top views of support element 18*d* removed from sole structure 12. Support element 18*d* includes two retaining band grooves 36*d* and 37*d* connected by an additional groove 38*d*. Each of grooves 36*d*, 37*d*, and 38*d* includes a recessed floor (39*d*, 41*d*, 43*d*) surrounded by side walls (40*d*, 42*d*, 44*d*). Recessed floor 43*d* may be slightly deeper than portions of floors 39*d* and 41*d* outside of the intersections of grooves 36*d* and 37*d* with groove 38*d*. A narrowed top portion 49*d* of support element 18*d* is defined by a shoulder 50*d* and an inset wall 51*d*. Shoulder 50*d* and inset wall 51*d* surround the perimeter of the top portion of element 18*d*. Narrowed top portion 49*d* nests snugly within cavity 27*d* of position 23*d*. The outline of inset wall 51*d* has a shape that corresponds to the shape of the outline of side wall 28*d*, the top face 52*d* of element 18*d* has a contour that corresponds to the contour of interior surface 33*d*, and the heights of inset wall 51*d* and side wall 28*d* at locations along their boundaries are matched so that top face 52*d* may contact interior surface 33*d*. When support element 18*d* is installed on base 17 in position 23*d*, bands 19*d* and 20*d* respectively rest within grooves 36*d* and 37*d*.

FIGS. 5E1 and 5E2 are respective bottom and top views of support element 18*e* removed from sole structure 12. Support element 18*e* includes two retaining band grooves 36*e* and 37*e* connected by an additional groove 38*e*. Each of grooves 36*e*, 37*e*, and 38*e* includes a recessed floor (39*e*, 41*e*, 43*e*) surrounded by side walls (40*e*, 42*e*, 44*e*). Recessed floor 43*e* may be slightly deeper than portions of floors 39*e* and 41*e* outside of the intersections of grooves 36*e* and 37*e* with groove 38*e*. A narrowed top portion 49*e* of support element 18*e* is defined by a shoulder 50*e* and an inset wall 51*e*. Shoulder 50*e* and inset wall 51*e* surround the perimeter of the top portion of element 18*e*. Narrowed top portion 49*e* nests snugly within cavity 27*e* of position 23*e*. The outline of inset wall 51*e* has a shape that corresponds to the shape of the outline of side wall 28*e*, the top face 52*e* of element 18*e* has a contour that corresponds to the contour of interior surface 33*e*, and the heights of inset wall 51*e* and side wall 28*e* at locations along their boundaries are matched so that top face 52*e* may contact interior surface 33*e*. When support element 18*e* is installed on base 17 in position 23*e*, bands 19*e* and 20*e* respectively rest within grooves 36*e* and 37*e*.

Each of support elements 18*b* through 18*e* can be installed in and removed from sole structure 12 in a manner similar to that described in connection with support element 18*a*. To remove one of support elements 18*b* through 18*e*, for example, retaining bands can be expanded (e.g., using the previously mentioned tool) and displaced from grooves of that support element so as to permit removal of that support element from its position on base 17. To install one of support elements 18*b* through 18*e*, bands can be expanded and allowed to contract into grooves of that support element while a narrowed top portion of that support element is pressed into a corresponding cavity of a support element position. Replacement support elements corresponding to each of positions 23 can be installed in a similar manner.

In some embodiments, each of support elements 18 may be formed from a material that provides cushioning. Examples of materials that may be used include compressible polymeric foams such as ethylene vinyl acetate (EVA).

Support elements may also or alternatively include other components or materials or combinations of other components and materials. In some embodiments, for example, a support element may include a fluid-filled bladder. As another example, a bottom of a support element may include a separate outsole element formed from one or more materials chosen to provide increased traction and/or resistance to abrasion. Examples of such materials include rubber compounds conventionally used for outsoles. A support element ground contacting surface may also include a tread pattern or other traction elements. A tread pattern and/or other traction elements may be formed directly in EVA or other cushioning material, may be formed in one or more outsole components attached to another part of a support element, or may be attached to a support element in another manner.

Figure 6:
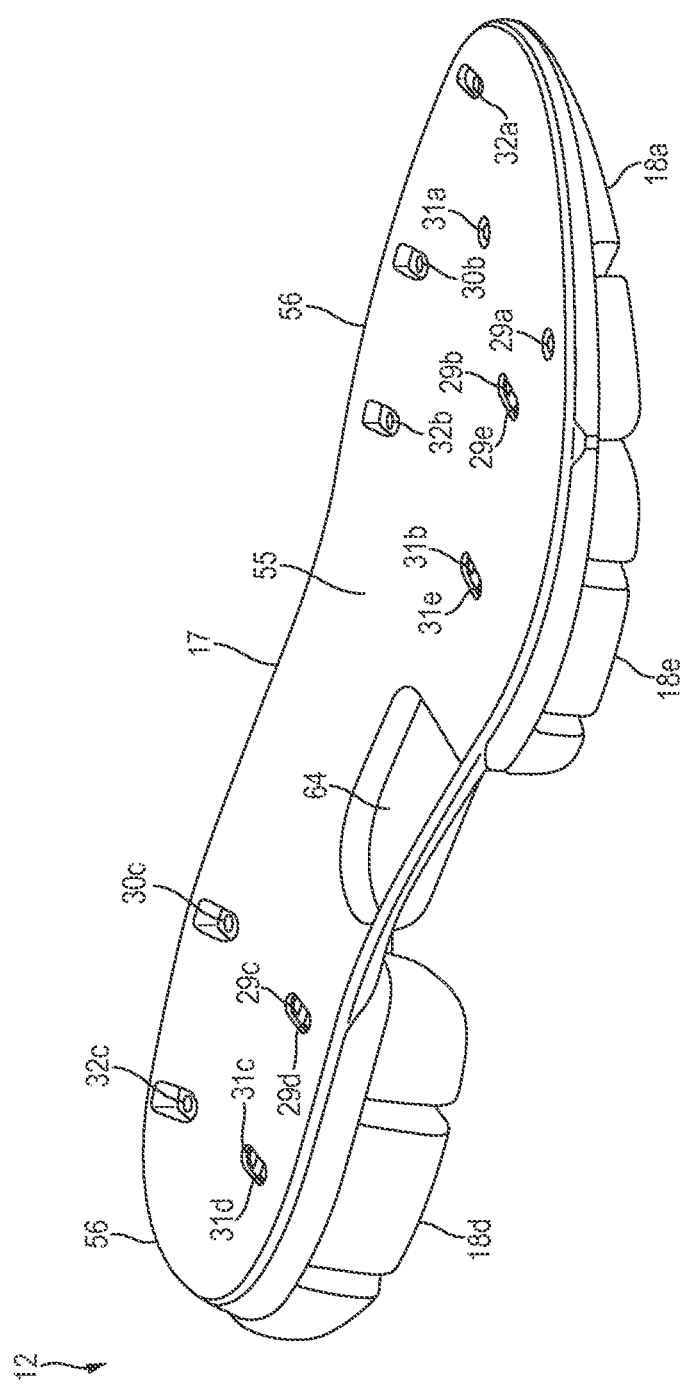
FIG. 6 is a front lateral perspective view of the sole structure of the shoe from FIG. 1, but with certain components removed.
Figure 7:
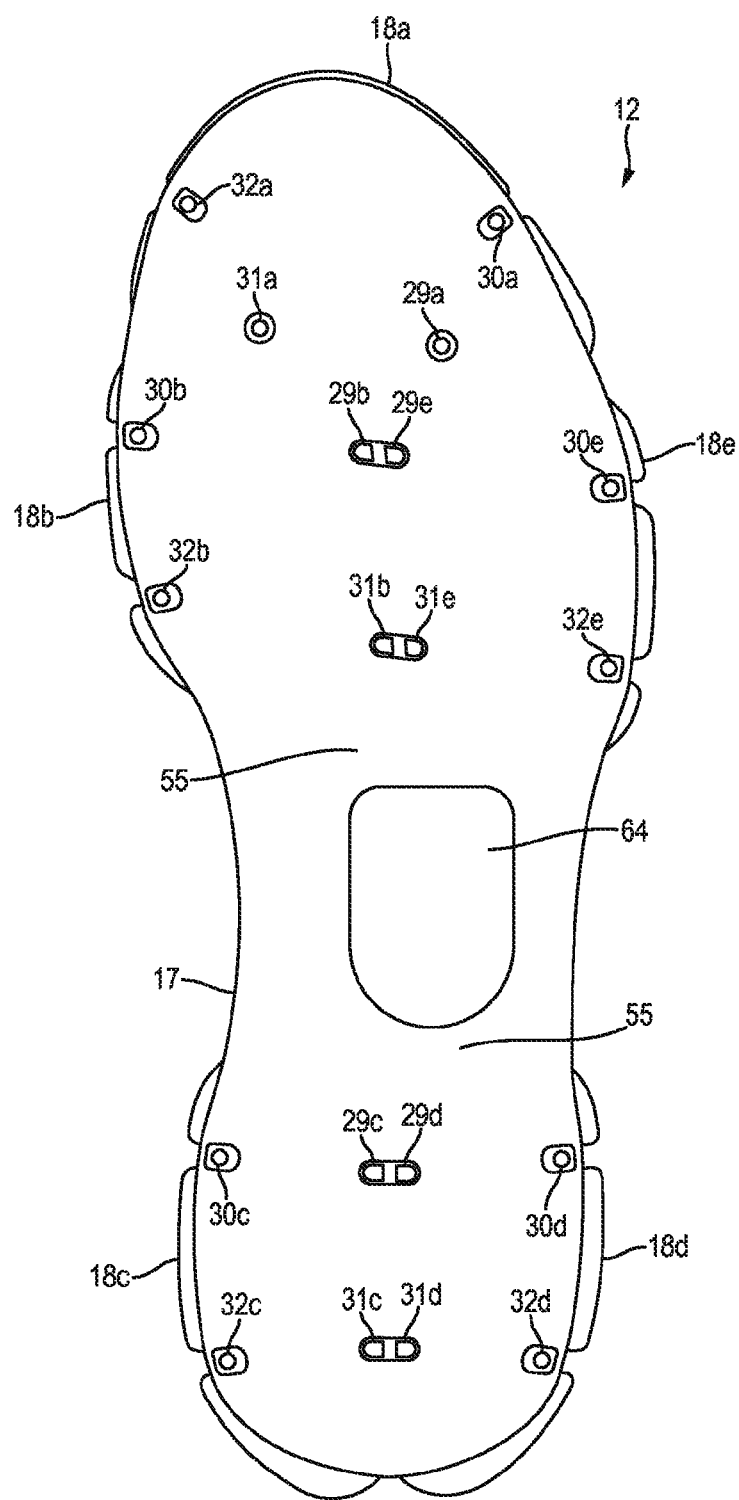
FIG. 7 is a top view of the sole structure of the shoe from FIG. 1, but with certain components removed.

FIG. 6 is a front lateral perspective view of sole structure 12. FIG. 6 is similar to FIG. 1, but with upper 11 and its attached lasting element removed. FIG. 7 is a top view of sole structure 12. Retaining bands 19 and retaining bands 20 have been omitted in FIGS. 6 and 7, as have a sensor assembly and electronics module that are described below. A top surface 55 of base 17 has a size and a shape approximately corresponding to a human foot outline. An outer edge 56 of base 17 extends upward from top surface 55. The contour of top surface 55 may be configured to generally correspond to the shape of the plantar region of a human foot and to provide arch support. In some embodiments, a separate midsole or other element may be interposed between a base such as base 17 and a lasting element of an upper. Top surface 55 includes a well 64 shaped to hold an electronics module, as described below.

Each of holes 29, holes 30, holes 31, and holes 32 extend from top surface 55 through base 17 to the underside thereof. Recesses are formed in regions of top surface 55 surrounding holes 29, holes 30, holes 31, and holes 32. Material at the ends of retaining bands 19 and retaining bands 20, and stops affixed to those ends, rest within some of the recesses so as to avoid creating bumps in the footbed of shoe 10, and so as to avoid bumps that would interfere with installation of the sensor assembly described below. In other recesses, a portion of retaining band material between two ends rests within the recess for similar reasons. A stop may be a knot in an end of a piece of retaining band material or may be a separate element attached to that end so as to prevent that end from pulling out through the bottom of base 17.

Retaining band 19a is formed by a single piece of elastic material that extends through holes 29a and 30a to create a loop on the bottom of base 17 in position 23a. Stops on the ends of that material piece rest within the recesses that surround holes 29a and 30a in top surface 55. Retaining band 20a is formed by a single piece of elastic material that extends through holes 31a and 32a to create a loop on the bottom of base 17 in position 23a, with stops on the ends of that material piece resting within the recesses that surround holes 31a and 32a in top surface 55.

A single piece of elastic material forms retaining bands 19b and 19e. That piece of material extends through hole 30b and out of the bottom side of base 17, back through hole 29b from the bottom side of base 17 to top surface 55, back through hole 29e from top surface 55 to the bottom side of base 17, and then back through hole 30e from the bottom side of base 17 to top surface 55. Stops on the ends of that material piece rest within recesses that surround holes 30b and 30e in top surface 55. A middle portion of that material piece rests within the recess that surrounds holes 29b and 29e in top surface 55. Retaining band 19b is the portion of that material piece creating a loop that extends between holes 29b and 30b in position 23b on the bottom side of base 17. Retaining band 19e is the portion of that material piece creating a loop that extends between holes 29e and 30e in position 23e on the bottom side of base 17.

Retaining bands 20b and 20e, retaining bands 19c and 19d, and retaining bands 20c and 20d are formed in a similar manner as retaining bands 19b and 19e. A single piece of elastic material passes through holes 32b, 31 b, 31e, and 32e to form retaining bands 20b and 20e as loops in positions 23b and 23e, respectively, on the bottom side of base 17. A single piece of elastic material passes through holes 30c, 29c, 29d, and 30d to form retaining bands 19c and 19d as loops in positions 23c and 23d, respectively, on the bottom side of base 17. A single piece of elastic material passes through holes 32c, 31c, 31d, and 32d to form retaining bands 20c and 20d in positions 23c and 23d, respectively, on the bottom side of base 17.

In other embodiments, retaining bands may be attached to a base in another manner. In some embodiments, for example, holes passing through a base plate may not be used. Instead, ends or intermediate portions of elastic material pieces may be glued or otherwise secured to a bottom surface of a base plate.

Figure 8:
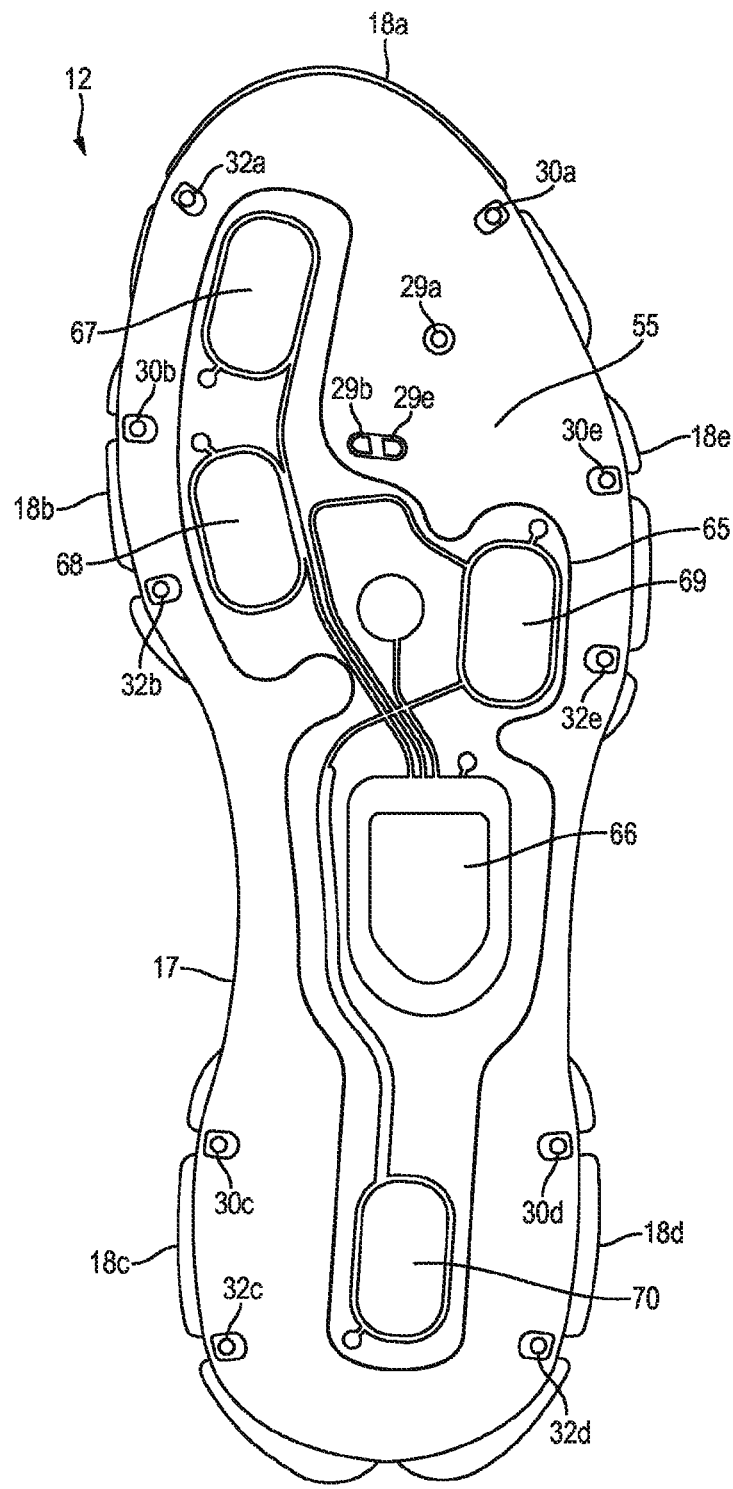
FIG. 8 is a top view of the sole structure of the shoe from FIG. 1, and with a sensor assembly and an electronics module included.

FIG. 8 is another top view of sole structure 12, but with a sensor assembly 65 and an electronics module 66 installed. Retaining bands 19 and retaining bands 20 have been omitted from FIG. 8. Sensor assembly 65 includes four sensors 67, 68, 69, 70 configured to measure force imposed by the foot of a shoe 10 wearer in a footbed region of shoe 10. Medial side forefoot sensors 67 and 68 are respectively located in regions approximately corresponding to the hallux (big toe) and to the head of the first metatarsal. Lateral side forefoot sensor 69 is located in a region approximately corresponding to the head of the fifth metatarsal. Heel sensor 70 is located in the heel region. In other embodiments, a sensor assembly may include more or fewer sensors and/or sensors may be placed in other locations.

Each of sensors 67 through 70 may, e.g., comprise electrodes separated by an air gap and/or by a force-sensitive resistor (FSR). Downward force on a sensor may increase current flow through (and voltage drop across) the sensor electrodes by increasing contact areas of the sensor electrodes and/or by reducing resistance of an FSR placed between the sensor electrodes. The increased current flow and/or reduced voltage may be measured by electronics module 66 and the measured value correlated to the amount of force being imposed on the sensor. In other embodiments, other types of sensors may also or alternatively be used.

Assembly 65 may further include sheets of polymer material to hold the electrodes and to hold leads that connect those electrodes to electronics module 66. The bottom side of sensor assembly 65 may be bonded directly to top surface 55. The top surface of sensor assembly 65, as well as surrounding regions of top surface 55 not covered by sensor assembly 65, may be bonded to the bottom of the lasting element stitched to upper 11.

Electronics module 66 includes a processor, memory, a power source, and other components described below in connection with FIG. 9. In some embodiments, electronics module 66 may be removable and replaceable. A flap may be cut in the portion of the lasting element attached to upper 11 located over well 64 and electronics module 66. After removing a sock liner, insole or other element within the void of upper 11, a user may pull back the flap in the lasting element to expose well 64 and electronics module 66.

In some embodiments, sensor assembly 65 and electronics module 66 may be a sensor system such as one of the sensor systems described in US patent application publication no. 2013/0213147, titled "Footwear Having Sensor System" and published Aug. 22, 2013 (U.S. patent application Ser. No. 13/401,918, filed Feb. 22, 2012), which publication and application in their entireties are incorporated by reference herein.

In some embodiments, a sensor assembly may be installed into a shoe in a different manner. As one example, a sensor assembly could be attached to a top surface of a base as in FIG. 8, but a foam layer or other type of midsole could be interposed between the top of a sensor assembly and the bottom of a lasting element attached to an upper. As another example, a sensor assembly could be embedded within a foam layer or other midsole element interposed between the top of a base such as base 17 and the bottom of a lasting element attached to an upper. As yet another example, a sensor assembly could be embedded in an insole or sock liner situated above a lasting element. In each of these examples, an opening could be formed in a midsole, sock liner or insole to permit access to an electronics module housed in a well such as well 64. Alternatively, an electronics module could be located elsewhere on a shoe.

Figure 9:
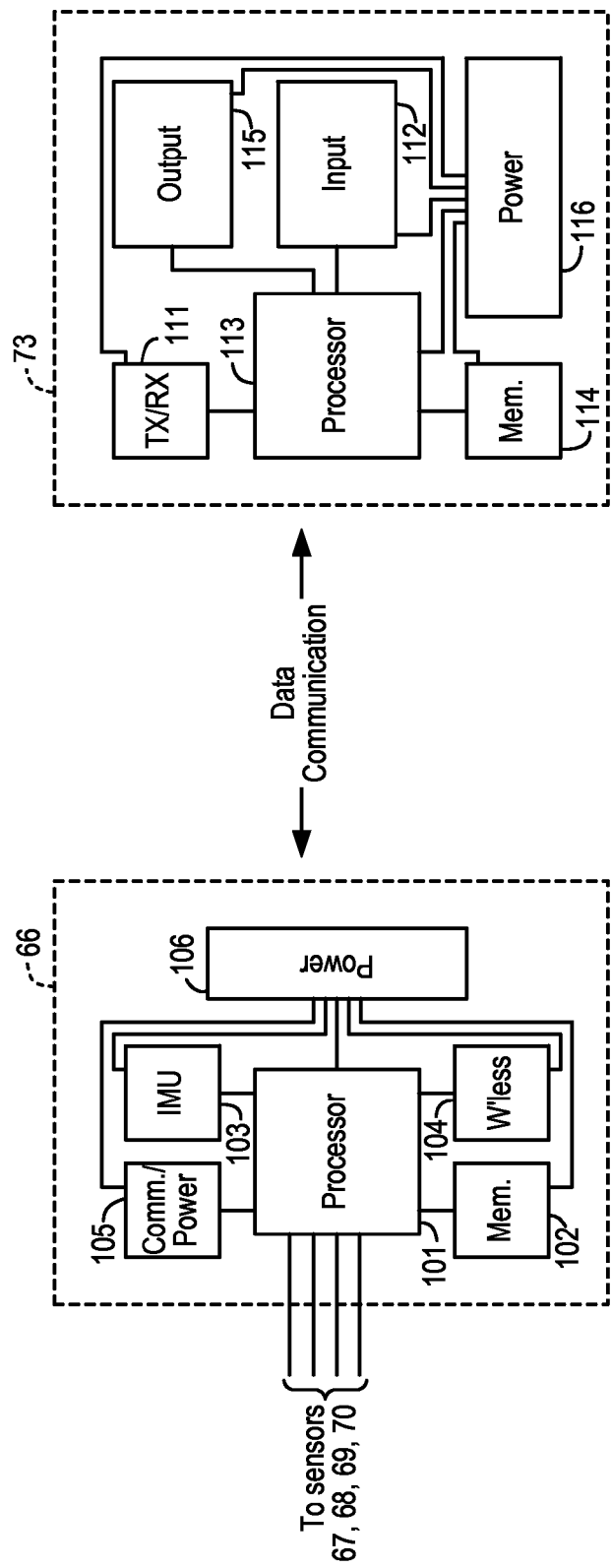
FIG. 9 is a block diagram of an electronics module of the shoe from FIG. 1 in communication with a second device.

FIG. 9 is a block diagram showing components of electronics module 66 and of a second device 73 with which electronics module 66 is in data communication. Second device 73 may be, e.g., a laptop computer, a tablet computer, a smart phone, or other type of device. Individual lines to or from blocks in FIG. 9 represent signal (e.g., data and/or power) flow paths and are not necessarily intended to represent individual conductors.

Electronics module 66 may include a processor 101, memory 102, an inertial measurement unit (IMU) 103, a low energy wireless communication module 104 (e.g., a BLUETOOTH communication chip), a communication and power transfer module 105, and a power source 106. Processor 101 receives inputs from each of sensors 67-70. Processor 101 executes instructions stored by memory 102 and/or stored in processor 101, which execution results in electronics module 66 performing operations such as are described herein. As used herein, "processor" or "a processor" refers to one or more microprocessors and/or other types of computational circuitry configured to perform operations such as are described herein, "instructions" may include hard-coded instructions and/or instructions that may be modified, and "memory" or "a memory" refers to one or more components (e.g., FLASH memory, RAM) able to store data in a non-transitory manner.

As indicated above, processor 101 is configured to receive inputs from sensors 67-70. As explained in more detail below, those inputs may be indicative of forces measured by sensors 67-70. As also explained below, processor 101 may be configured to transmit data that is based on the inputs received from sensors 67-70. In some embodiments, data based on the inputs received from sensors 67-70 may include data that indicates the forces measured by sensors 67-70. In some embodiments, data based on the inputs received from sensors 67-70 may also or alternatively include other types of data. Those other types of data may include data indicating one or more installed support elements that should be replaced and/or one or more replacement support elements.

Data stored in memory 102 and/or processor 101 may include an identifier for each of support elements 18, as well as data defining various parameters of each support element 18. Such parameters may include, without limitation, corresponding position 23 in which the support element is installed and values for one or more characteristics of the support element. Such characteristics may include, without limitation, compressibility, height, type of ground contact surface, etc. Data stored in memory 102 and/or processor 101 may also include values for forces or pressures measured by sensors 67-70, times for when such forces or pressures were measured, etc.

IMU 103 may include a gyroscope and/or an accelerometer and/or a magnetometer. Data output by IMU 103 may be used by processor 101 to detect changes in orientation and motion of a shoe containing controller electronics module 66, and thus of a foot wearing that shoe. Processor 101 may use such information to determine that a foot is experiencing a particular portion of a gait cycle (e.g., rolling from the lateral to the medial side as the wearer progresses through the step portion of the gait cycle), and may correlate gait cycle information with forces measured using sensors 67-70.

Wireless communication module 104 may include an ASIC (application specific integrated circuit) and be used to communicate programming and other instructions from second device 73 to processor 101, as well as to communicate data that may be stored by memory 102 or processor 101 to second device 73. For example, and as discussed below, module 104 may be used to receive data from second device 73 that includes identifiers for each of support elements 18 installed in sole structure 12, as well as data regarding characteristics of those support elements. As another example, module 104 may be used to transmit data to second device 73 that indicates forces measured during running and/or that recommends one or more of support elements 18 be replaced with a support element having different characteristics.

Communication and power transfer module 105 may include, e.g., a USB (Universal Serial Bus) port and associated circuitry. In some embodiments, module 105 may be connected to a USB cable and used to transfer the same data transferrable via wireless module 104. A connection to module 105 may also be used to charge a battery within power source 106. Power source 106 may also include circuitry to control charging and discharging of that battery.

Second device 73 may be used to communicate with electronics module 66. As indicated above, second device 73 may be, e.g., a smart phone, a tablet computer, a laptop computer, or other type of device having data storage and processing capability. Device 73 may include a transceiver module 111, a user input device 112, a processor 113, a memory 114, an output device 115, and a power source 116. A transceiver module may be a wireless communication module (e.g., a BLUETOOTH module), a USB port and associated circuitry, and/or other component or components that facilitate data transfer. User input device 112 may be a touchscreen, a keyboard, a mouse, etc. Output device 115 may be a display screen, a speaker, a printer, or other device that physically communicates information in a form that can be understood by a human. Power source 116 may include a battery. Processor 113 may execute instructions stored in memory 114 and/or within processor 113 to carry out operations such as receiving communications from electronics module 66, analyzing data received from electronics module 66, generating graphical and/or video and/or audio information based on data received from electronics module 66, presenting that generated information through output device 115, receiving user input via device 112, and communicating data to electronics module 66 based on that user input.

A shoe such as shoe 10 offers numerous advantages and opportunities for customization to match preferences and/or needs of a particular individual. For each of positions 23a through 23e on base 17, there may be numerous corresponding support elements that can potentially be installed, with each of those support elements varying from the others based on one or more characteristics.

One such support element characteristic may be the degree of cushioning provided. A soft support element corresponding to a particular position on base 17 may be highly compressible and provide a high degree of cushioning. A firm support element corresponding to that same position may be much less compressible and provide substantially less cushioning. Other support elements corresponding to that position may provide different degrees of cushioning that are greater than that of the firm support element but less than that of the soft support element. The different degrees of cushioning could be provided by, e.g., utilizing different densities of EVA or other foam material used to form the cushioning elements, utilizing a bladder and/or different types of bladders, utilizing different combinations of multiple of foam types, utilizing different combinations of multiple of bladder types, utilizing different combinations of foam types and bladder types, etc.

In addition to varying the overall amount of cushioning provided by different support elements corresponding to a particular position on base 17, support elements may vary based on the distribution of cushioning. For example, a first support element may be firmer on a lateral side of the element than on a medial side of the element, a second support element may be firmer on the medial side than on the lateral side, a third support element may be firmer in a front of the element than in a rear of the element, etc.

Another support element characteristic may be height. A first support element corresponding to a particular position on base 17 may have a narrowed top portion that fits within the cavity of the corresponding position, and a remainder having a height h1. A second support element corresponding to that same position may have a narrowed top portion identical to that of the first support element, but the remainder of the second support element may have a height h2 that is less than h1. Additional support elements may have other heights.

Another support element characteristic may be type of ground contacting surface. For example, a first support element corresponding to a particular position on base 17 may have a first type of ground contacting surface formed from a first outsole material that provides higher friction but that is more susceptible to abrasion on concrete. A second support element corresponding to that same position may have a second type of ground contacting surface formed from a second outsole material that is less susceptible to abrasion on concrete, but that provides less friction. A third support element corresponding to that same position may have a tread pattern optimized for trail running. A fourth support element corresponding to that same position may have a tread pattern optimized for running on a track or indoors.

The above characteristics merely represent some examples. Support elements can also be varied based on additional characteristics. Moreover, support elements corresponding to a particular position on base 17 may vary based on different combinations of characteristics. For example, a first support element may be firm and have a first tread pattern and/or first outsole material, a second support element may be less firm and have less height than the first support element and have a second tread pattern and/or second outsole material.

Figure 10A:
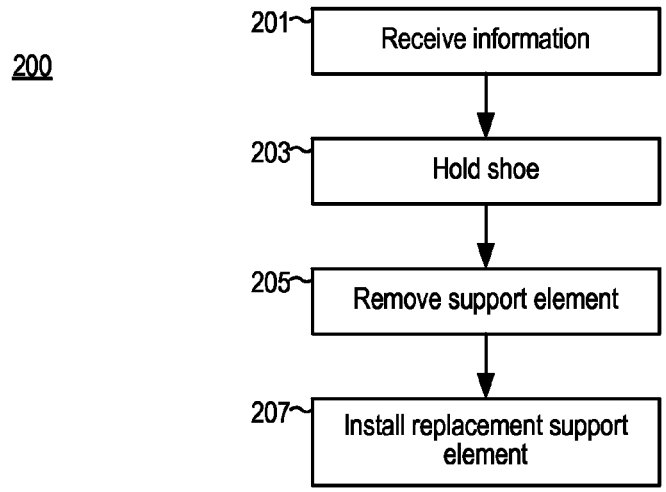
FIG. 10A is a block diagram showing steps in a method according to some embodiments.

FIG. 10A is a block diagram showing steps performed in a method 200 according to some embodiments. In method 200, a support element installed in a sole structure is identified, removed, and replaced with a replacement support element. The sole structure may be part of a shoe that includes an upper and the sole structure, with the sole structure including multiple independent support elements located in a plantar region, and with each of the support elements at least partially secured in a corresponding position in the sole structure by at least one retaining band that surrounds at least a portion of the support element. For convenience, method 200 is described by example of removing support element 18b from shoe 10 and replacing element 18b with a replacement support element. However, method 200 may be performed in connection with other support elements 18 and in connection with shoes and support elements according to other embodiments.

In a first step 201, information is received that identifies a support element installed in a sole structure, and that further identifies a replacement support element. The installed support element may be identified specifically or by position in which that support element is currently installed. In the present example, the information received in step 201 identifies support element 18b and a replacement support element to be installed once support element 18b is removed.

In step 203, shoe 10 is held in preparation for removal of the identified support element. In some embodiments, method 200 may be performed by a wearer of shoe 10 while shoe 10 remains on the wearer's foot. For example, a wearer of shoe 10 may sit on a bench and place the lateral side of the wearer's right foot on the wearer's left knee. In this manner, a seated wearer could easily access the bottom of sole structure 12. In other embodiments, a performer of method 200 may be an individual who has removed shoe 10 from his or her foot and/or who is planning to place shoe 10 onto his or her foot after replacement of support element 18b. In still other embodiments, a performer of method 200 may be an individual (e.g., a coach or trainer) performing the operations of method 200 for another person who is wearing (or who is about to wear) shoe 10.

In step 205, support element 18b is removed from sole structure 12. As part of this removal, retaining bands 19b and 20b securing support element 18b in position 23b are expanded and moved out of grooves 36b and 37b. For example, a screw driver tip or the tip of another tool may be placed under retaining band 20b. The tool may then be used to pull retaining band 20b out of groove 37b. Once out of groove 37b, band 20b may be rolled and/or slid over the rear end of support element 18b In a similar manner, the tool then may be used to pull retaining band 19b out of groove 36b. With expanded retaining band 19b resting on the front end of support element 18b forward of groove 36b, the rear end of support element 18b may be lifted away from plate 17 and the front end of support element 18b pulled out of expanded band 19b.

In step 207, the replacement support element is installed into the position vacated by the support element removed in step 205. In the current example, the replacement support element is configured for installation in position 23b. In particular, the replacement support element may have a narrowed top portion configured to rest within cavity 27b of position 23b. The remainder of the replacement support element also has a shape similar to that of removed support element 18b, including two corresponding grooves similar to grooves 19b and 20b. However, the replacement support element may differ from removed support element 18b with regard to one or more characteristics. For example, the replacement support element may be firmer or softer than removed support element 18b.

As part of installing the replacement support element, retaining bands 19b and 20b are expanded and allowed to contract into corresponding grooves of the replacement support element. For example, the band 19b may be expanded by pulling outward on band 19b, a front end of the replacement support pushed into the expanded loop of expanded band 19b, and expanded band 19b pulled onto the front end of the replacement support element. Before allowing the narrowed top portion of the replacement support element to fully seat within cavity 27b of position 23b, band 20b may be pulled out and over the rear end of the replacement support element. Bands 19b and 20b may then be moved into their corresponding grooves and allowed to contract, thereby securing the replacement support element in position 23b.

In the embodiment of shoe 10, each of support elements 18 is secured in place by two retaining bands. In other embodiments, a support element may be secured by a single retaining band. In such embodiments, steps 205 and 207 of method 200 may be performed by expanding and moving that single band. In still other embodiments, a support element may be secured by more than two retaining bands. In those embodiments, steps 205 and 207 may be performed by expanding and moving more than two bands.

Referring back to step 201, a support element installed in a sole structure and a replacement support element may be identified for replacement in various ways. After walking and/or running while wearing shoe 10 with all support elements 18 installed, for example, the wearer may identify one or more support elements 18 for replacement based on the feel of shoe 10 and may select the next firmer (or next softer) support element available for the same position. As another example, a coach or trainer may observe the performance of a shoe 10 wearer while walking or running, and may identify one or more of support elements 18 for replacement based on those observations. As yet another example, electronics module 66 and/or another device (e.g., second device 73 in FIG. 9) may analyze data collected using sensor assembly 65, and based on that analysis may generate data that identifies and/or may be used to identify one or more support elements to be replaced and/or the replacement support elements to be used.

Figure 10B:
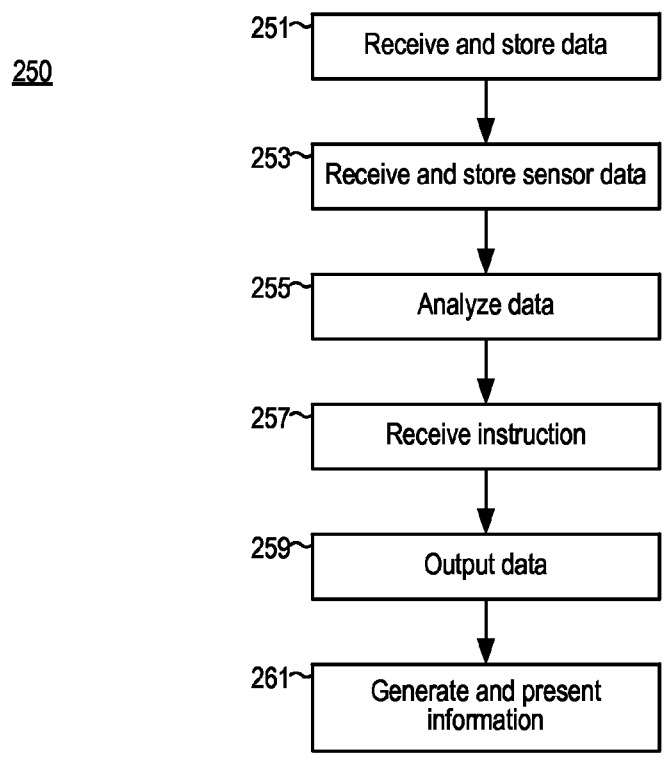
FIG. 10B is a block diagram showing steps in a method according to some additional embodiments.

FIG. 10B is a block diagram showing operations performed in a method 250 according to some embodiments. In method 250, processor 101 of electronics module 66 receives inputs from sensors 67-70 while a wearer of shoe 10 (with support elements 18a-18e installed) walks and/or runs. Processor 101 then evaluates data based on those inputs and recommends one or more of support elements 18 for replacement.

In step 251, processor 101 receives and stores data in memory 102, which data includes identifiers for each of support elements 18a through 18e and which indicates which of positions 23 is occupied by each of support elements 18. Processor 101 may receive data in step 251, via wireless module 104 and/or module 105 from second device 73, after a user provides input via input device 112.

In step 253, processor 101 receives inputs from sensors 67-70 while a shoe 10 wearer walks and/or runs. Inputs from each of sensors 67-70 may represent forces experienced in a region of the shoe 10 footbed corresponding to that sensor. Processor 101 then stores data based on those sensor inputs. That stored data may include, for each sensor, a maximum force measured by that sensor during each gait cycle.

In step 255, processor 101 analyzes the data stored in step 253 and identifies any of support elements 18a through 18e that should potentially be replaced. Step 255 can be performed in numerous different ways. In some embodiments, for example, processor 101 may determine an average maximum force value for each of sensors 67-70. The average force may be calculated by, e.g., summing the maximum forces measured by a sensor during N gait cycles and then dividing that sum by N. Processor 101 may then identify, based on the previously-stored data identifying support elements 18a through 18e installed in sole structure 12, data in memory 102 that includes a look up table for each of sensors 67-70. For each of sensors 67-70, processor 101 may compare the average maximum force value calculated for that sensor to values or value ranges in the identified look-up table and determine if one or more of support elements 18 corresponding to the location of that sensor should be replaced. For example, an average maximum force within a certain range may correlate to a support element 18 being compressed an appropriate amount, and may indicate no replacement is necessary. An average maximum force value above that range may correlate to the support element being overcompressed, and may indicate that the support element should be replaced with a firmer support element. An average maximum force value below that range may correlate to the support element being undercompressed, and may indicate that the support element should be replaced with a softer support element. Each of the look-up tables could be developed using compressibilities of materials from which support elements are formed and known geometries of the support elements, and/or by experiment. The foregoing merely represents one way in which step 255 may be performed. In other embodiments, step 255 may include one or more alternate and/or additional operations.

In step 257, processor 101 receives an instruction to output data generated in step 255. The instruction may be received from second device 73 via module 104 and/or via module 105. In response, and as shown in step 259, processor 101 may output data generated in step 255 by transmitting that data to second device 73 via module 104 and/or module 105. Upon receiving that transmitted data, processor 113 of second device 73 may generate and present information on display device 115 indicating which of support elements 18 should be replaced and the type of support element to be used as a replacement (step 261). The information may be presented in a form understandable to a human. For example, processor 113 may generate a graphic on a display screen that depicts support elements 18 and highlights one or more of those support elements to indicate those one or more support elements should be replaced, and that includes text identifying one or more suggested replacement support elements for each of the highlighted support elements.

Figure 10C:
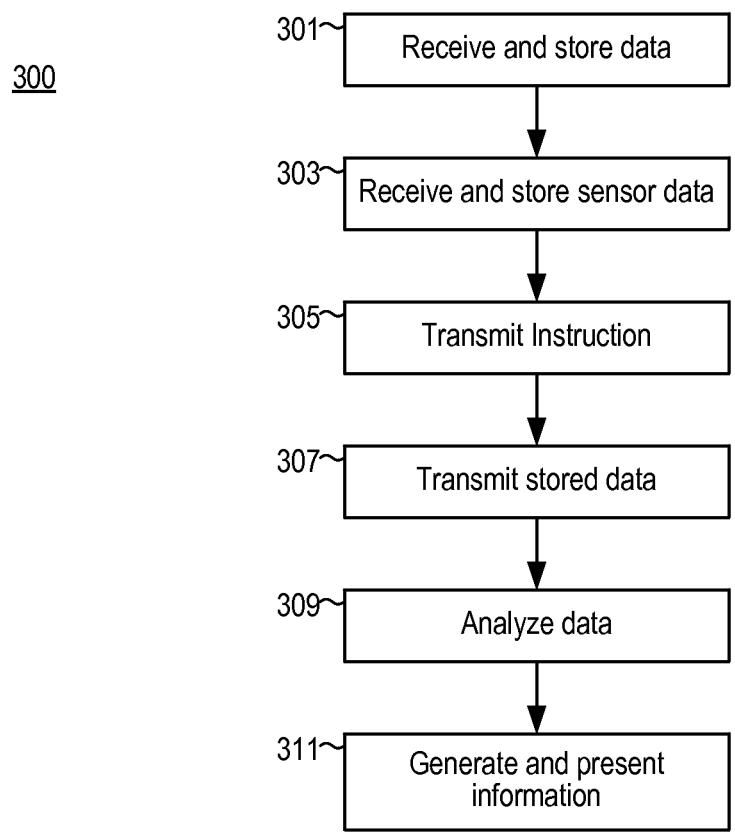
FIG. 10C is a block diagram showing steps in a method according to some further embodiments.

FIG. 10C is a block diagram showing operations performed in a method 300 according to some embodiments. Method 300 is similar to method 250, but with certain operations performed by second device 73 instead of by electronics module 66. In step 301, processor 113 of second device 73 receives and stores in memory 114 data providing identifiers for each of support elements 18a through 18e and indicating which of positions 23 is occupied by each of support elements 18. In step 303, processor 101 of electronics module 66 receives input from sensors 67-70 while a shoe 10 wearer walks and/or runs and stores data, which stored data may include data similar to that stored in step 253 of method 250. In step 305, processor 113 of second device 73 transmits an instruction to electronics module 66 to transmit the data stored in step 303. In step 307, and in response to receiving the instruction transmitted in step 305, processor 101 of electronics module 66 transmits that stored data to second device 73 via module 104 and/or module 105. In step 309, and in response to receiving the data transmitted in step 307, processor 113 of second device 73 stores the received data in memory 114, analyzes that data, identifies any of support elements 18a through 18e that should potentially be replaced, and identifies a replacement support element for each of support elements 18a through 18e identified for potential replacement. Operations performed by processor 113 in step 309 may be similar to those performed by processor 101 in step 255 of method 250. In step 311, and similar to step 261 of method 250, processor 113 may generate and present information on display device 115 indicating which of support elements 18 should be replaced and the type of support element to be used as a replacement for each of the indicated support elements 18.

Figure 11:
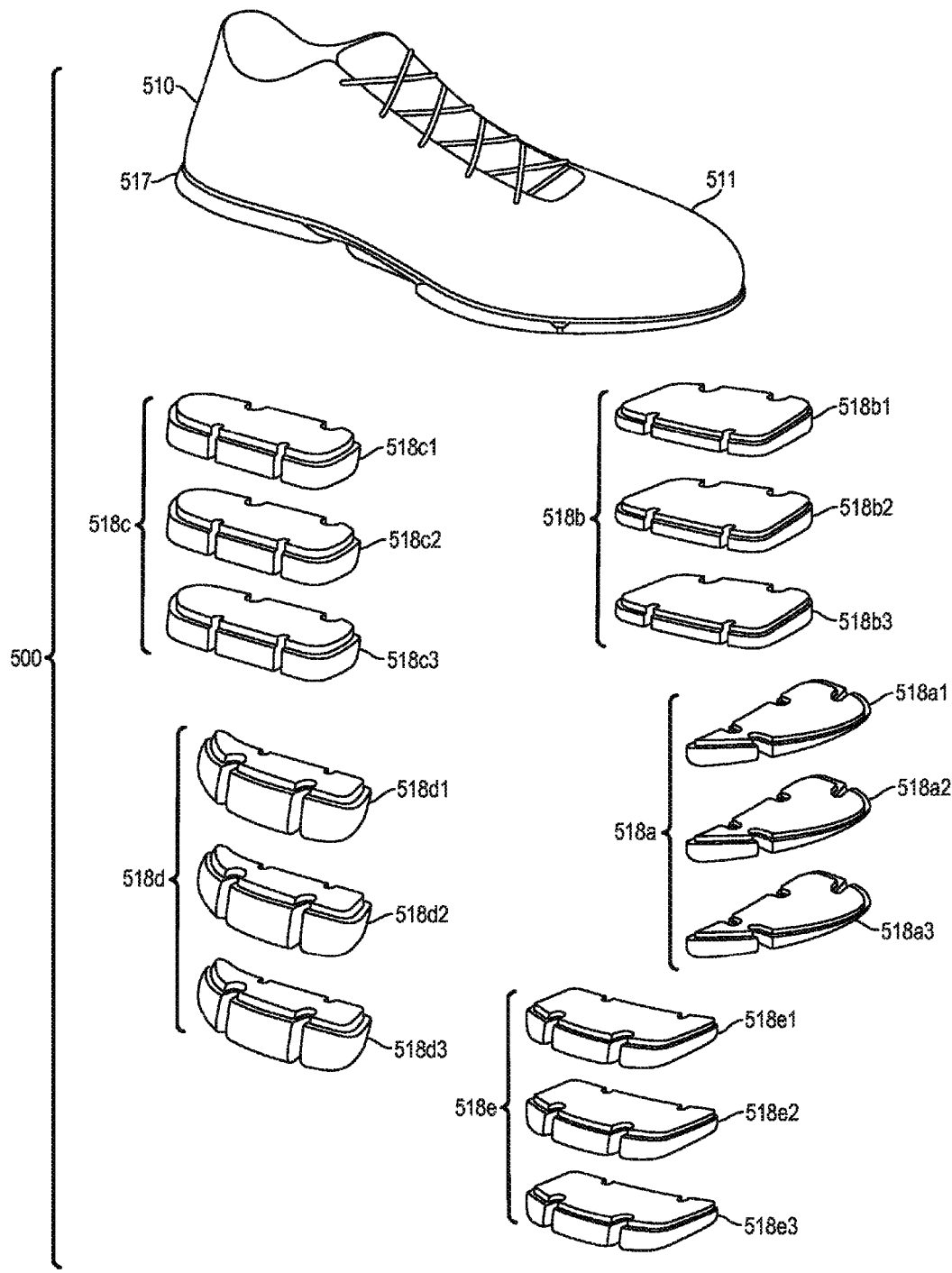
FIG. 11 shows a kit according to some embodiments.

In some embodiments, a shoe such as shoe 10 may be provided as part of a kit. In particular, that shoe may provided with multiple support elements from which a user can select a support element for installation into a first position, multiple support elements from which a user can select a support element for installation into a second position, etc. FIG. 11 shows a kit 500 according to one such embodiment. Kit 500 includes a shoe 510. Shoe 510 has a base 517 that is substantially identical to base 17 of shoe 10 and an upper 511 that is substantially identical to upper 11 of shoe 10. Although not visible in FIG. 11, shoe 510 also includes a sensor assembly that is substantially identical to sensor assembly 65 of shoe 10 and that is installed in shoe 510 in a manner substantially identical to the manner in which sensor assembly 65 is installed in shoe 10. Similarly, shoe 510 also includes an electronics module that is substantially identical to electronics module 66 of shoe 10 and that is installed in shoe 510 in a manner substantially identical to the manner in which electronics module 66 is installed in shoe 10.

Kit 500 includes a kit 518a of three toe forefoot support elements 518a1, 518a2, and 518a3, each of which is installable in a toe forefoot position of base 517 that is substantially identical to toe forefoot position 23a of base 17. Support element 518a1 may be firmer than support element 518a2, which may be firmer than support element 518a3. Kit 500 also includes a kit 518b of three medial forefoot support elements 518b1, 518b2, and 518b3, each of which is installable in a medial forefoot position of base 517 that is substantially identical to medial forefoot position 23b of base 17. Support element 518b1 may be firmer than support element 518b2, which may be firmer than support element 518b3. Kit 500 further includes a kit 518c of three medial heel support elements 518c1, 518c2, and 518c3, each of which is installable in a medial heel position of base 517 that is substantially identical to medial heel position 23c of base 17. Support element 518c1 may be firmer than support element 518c2, which may be firmer than support element 518c3. Kit 500 additionally includes a kit 518d of three lateral heel support elements 518d1, 518d2, and 518d3, each of which is installable in a lateral heel position of base 517 that is substantially identical to lateral heel position 23d of base 17. Support element 518d1 may be firmer than support element 518d2, which may be firmer than support element 518d3. Kit 500 furthermore includes a kit 518e of three lateral forefoot support elements 518e1, 518e2, and 518e3, each of which is installable in a lateral forefoot position of base 517 that is substantially identical to lateral forefoot position 23e of base 17. Support element 518e1 may be firmer than support element 518e2, which may be firmer than support element 518e3.

In other embodiments, a kit may include one or more sub-combinations and/or other variations of the components shown in FIG. 11. In some embodiments, for example, the support elements configured for a particular position on base 517 may also or alternatively vary based on characteristics other than compressibility. Examples of such other characteristics are previously described. In some embodiments, a kit may include more than three or less than three support elements configured for a particular position on base 517. In some embodiments, kit 518a (support elements 518a1-518a3), kit 518b (support elements 518b1-518b3), kit 518c (support elements 518c1-518c3), kit 518d (support elements 518d1-518d3), and/or kit 518e (support elements 518e1-518e3) may be included in a kit that does not include shoe 510. In some embodiments, shoe 510 may be provided with a default set of support elements that includes a single support element installed in each of the positions of base 517. One or more kits may then provide multiple replacement support elements for one, some, or all of the positions on base 517.

Other embodiments include numerous additional variations on the components and combinations described above. Without limitation, such variations may include one or more of the following.

In some embodiments, support elements may have other arrangements. As but one example, a heel region of a sole structure base may be configured to receive a single support element instead of two support elements. As but another example, a lateral forefoot region of a sole structure base may be configured to receive two support elements instead of a single support element and/or a medial forefoot region of a sole structure base may be configured to receive two support elements instead of a single support element. As yet another example, support elements could be configured so that a majority of an installed forefoot region support element is located on a medial side of a shoe centerline, but with a portion of that forefoot region support element extending into the lateral side of the shoe centerline. That configuration may also or alternatively include another forefoot region support element that, when installed, has a majority of its area located on a lateral side of a shoe centerline, but with a portion of that forefoot region support element extending into the medial side of the shoe centerline.

In some embodiments, support elements may have other shapes. For example, and as indicated in the preceding paragraph, some embodiments may have more or less support elements in a particular region and/or support elements configured to cover sole structure regions in a manner other than as shown in connection with shoe 10. As but another example, support elements may include additional grooves to increase flexibility.

In some embodiments, a single support element may be replaceable with multiple support elements, and/or vice versa. For example, in some embodiments medial forefoot support element 18b might be replaceable with two replacement support elements. A first of those replacement support elements may correspond to the front portion of medial forefoot position 23b and may be securable using retaining band 19b. A second of those replacement support elements may correspond to the rear portion of medial forefoot position 23b and may be securable using retaining band 20b.

Such a configuration could be useful if, e.g., a wearer of shoe 10 wished to separately adjust firmness in the front and rear portions of the medial forefoot region corresponding to position 23b. A similar one-for-multiple or multiple-for-one replacement scheme could be provided for other positions 23.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from practice of various embodiments. The embodiments discussed herein were chosen and described in order to explain the principles and the nature of various embodiments and their practical application to enable one skilled in the art to utilize the present invention in various embodiments and with various modifications as are suited to the particular use contemplated. Any and all combinations, sub-combinations and permutations of features from herein-described embodiments are within the scope of the invention. In the claims, a reference to a potential or intended wearer or a user of a component does not require actual wearing or using of the component or the presence of the wearer or user as part of the claimed invention.

The invention claimed is:

1. An article of footwear comprising:
   an upper;
   a plurality of sensors positioned within the article of footwear and configured to measure force exerted in a footbed region of the article of footwear;
   a processor communicatively coupled to the sensors, wherein the processor is configured to receive input indicative of forces measured by the sensors and to transmit data based on the input indicative of forces measured by the sensors; and
   a sole structure including a plurality of support elements located in a plantar region, wherein each of the support elements is non-destructively removable from and replaceable into the sole structure.

2. The article of footwear of claim 1, wherein the data based on the input indicative of forces measured by the sensors comprises data indicative of forces measured by the sensors.

3. The article of footwear of claim 1, wherein the data based on the input indicative of forces measured by the sensors comprises data indicating a support element of the plurality that should be replaced.

4. The article of footwear of claim 1, wherein each of the support elements is independently and non-destructively removable from and replaceable into the sole structure from an exterior underside of the article.

5. The article of footwear of claim 1, wherein each of the support elements is at least partially secured in a corresponding position on the sole structure by a corresponding retaining band surrounding at least a portion of the support element, and wherein each of the retaining bands is elastically and non-destructively expandable.

6. The article of footwear of claim 1, wherein the plurality of support elements includes a medial side support element and a lateral side support element.

7. The article of footwear of claim 6, wherein the medial side support element and the lateral side support element are located in a forefoot region.

8. The article of footwear of claim 7, wherein the plurality of support elements includes a medial side support element in a heel region and a lateral side support element in the heel region.

9. The article of footwear of claim 1, wherein surfaces of the support elements are positioned to be ground contact surfaces when the article is worn.

10. The article of footwear of claim 1, wherein the sole structure further comprises a base, and wherein each of the support elements includes a portion resting within a corresponding cavity formed in a bottom side of the base.

11. The article of footwear of claim 1, wherein the plurality of support elements comprises one or more forefoot support elements covering substantially all of a forefoot region and forming substantially an entire ground contacting surface in the forefoot region.

12. The article of footwear of claim 1, wherein the plurality of support elements comprises one or more heel support elements covering substantially all of a heel region and forming substantially an entire ground contacting surface in the heel region.

13. The article of footwear of claim 12, wherein the plurality of support elements comprises one or more forefoot support elements covering substantially all of a forefoot region and forming substantially an entire ground contacting surface in the forefoot region.

14. A method comprising:
   receiving a data transmission from an article of footwear, wherein
      the article of footwear comprises an upper, a plurality of sensors positioned within the article of footwear and configured to measure forces exerted in a footbed region of the article of footwear, and a processor,
      the processor is communicatively coupled to the sensors,
      the processor is configured to receive input indicative of forces measured by the sensors and to transmit data based on the input indicative of forces measured by the sensors, and
      the article of footwear comprises a sole structure including a plurality of support elements located in a plantar region, each of the support elements being non-destructively removable from and replaceable into the sole structure;
   identifying, in response to the received data transmission, a support element of the plurality for replacement;
   removing the identified support element from the article of footwear; and
   replacing the removed support element with a replacement support element.

15. The method of claim 14, wherein the received data transmission includes data indicating the support element of the plurality, and wherein the identifying comprises generating and presenting information indicating the support element of the plurality.

16. The method of claim 14, wherein the received data transmission includes data indicating forces measured by the sensors during wear of the article on a wearer foot, and wherein the identifying comprises analyzing data of the received data transmission to determine the support element of the plurality and generating and presenting information indicating the support element of the plurality.

17. The method of claim 14, wherein the identified support element is at least partially secured in position on the sole structure by a retaining band surrounding at least a portion of the identified support element, and wherein the retaining band is elastically and non-destructively expandable.

18. The method of claim 14, wherein the replacement support element has a compressibility characteristic that is different from a compressibility characteristic of the removed support element.

19. The method of claim 14, wherein the removing and replacing are performed while the article of footwear is worn on the wearer foot.

20. A kit comprising:
an article of footwear comprising an upper, a sole structure base having a plurality of positions defined therein, a plurality of sensors positioned within the article of footwear and configured to measure forces exerted in a footbed region of the article of footwear, and a processor, wherein the processor is communicatively coupled to the sensors and configured to receive input indicative of forces measured by the sensors and to transmit data based on the input indicative of forces measured by the sensors;
a plurality of first position support elements corresponding to a first of the positions, each of the first position support elements configured for placement into, securing in, and non-destructive removal from the first position; and
a plurality of second position support elements corresponding to a second of the positions, each of the second position support elements configured for placement into, securing in, and non-destructive removal from the second position.

21. The kit of claim 20, wherein
each of the first position support elements is configured for placement into the first position and for securing in the first position by a first retaining band coupled to the base and corresponding to the first position, wherein the first retaining band is elastically and non-destructively expandable, and
each of the second position support elements is configured for placement into the second position and for securing in the second position by a second retaining band coupled to the base and corresponding to the second position, wherein the second retaining band is elastically and non-destructively expandable.

22. The kit of claim 20, wherein
one of the first position support elements has a compressibility characteristic different from a compressibility characteristic of another of the first position support elements, and
one of the second position support elements has a compressibility characteristic different from a compressibility characteristic of another of the second position support elements.

23. The kit of claim 20, wherein each of the positions comprises a cavity formed in the base.

24. The kit of claim 20, wherein the first position is on a medial side of the sole structure base and the second position is on a lateral side of the sole structure base.

25. The kit of claim 20, wherein the first position is on a medial side of the sole structure base in a forefoot region, the second position is on a lateral side of the sole structure base in the forefoot region, and the plurality of positions include a third position in a heel region, and further comprising:
a plurality of third position support elements corresponding to a third of the positions, each of the third position support elements configured for placement into, securing in, and non-destructive removal from the third position.

* * * * *

UNITED STATES PATENT AND TRADEMARK OFFICE
CERTIFICATE OF CORRECTION

| | |
|---|---|
| PATENT NO. | : 9,635,901 B1 |
| APPLICATION NO. | : 14/887769 |
| DATED | : May 2, 2017 |
| INVENTOR(S) | : Morrison et al. |

It is certified that error appears in the above-identified patent and that said Letters Patent is hereby corrected as shown below:

On the Title Page

Item (22) Filed Line 1:
After "2015", insert --¶(65) Prior Publication Data
US 2017/0105476 A1 Apr. 20, 2017--

Signed and Sealed this
First Day of August, 2023

Katherine Kelly Vidal
*Director of the United States Patent and Trademark Office*